(12) United States Patent  
Gonnelli et al.

(10) Patent No.: US 9,125,983 B2  
(45) Date of Patent: *Sep. 8, 2015

(54) HYDRAULICALLY ACTUATED PUMP FOR FLUID ADMINISTRATION

(75) Inventors: Robert R. Gonnelli, Mahwah, NJ (US); Devin V. McAllister, Shrewsbury, MA (US); Steven F. Levesque, North Pembroke, MA (US)

(73) Assignee: VALERITAS, INC., Bridgewater, NJ (US)

( * ) Notice: Subject to any disclaimer, the term of this patent is extended or adjusted under 35 U.S.C. 154(b) by 556 days.

This patent is subject to a terminal disclaimer.

(21) Appl. No.: 12/762,307

(22) Filed: Apr. 17, 2010

(65) Prior Publication Data

US 2010/0217191 A1 Aug. 26, 2010

Related U.S. Application Data

(63) Continuation of application No. 12/336,363, filed on Dec. 16, 2008, now Pat. No. 8,070,726, which is a continuation of application No. 10/831,354, filed on Apr. 23, 2004, now Pat. No. 7,530,968.

(60) Provisional application No. 60/465,070, filed on Apr. 23, 2003.

(51) Int. Cl.
*A61M 37/00* (2006.01)
*A61M 5/145* (2006.01)
(Continued)

(52) U.S. Cl.
CPC ........... *A61M 5/1452* (2013.01); *A61M 1/1032* (2014.02); *A61M 5/155* (2013.01);
(Continued)

(58) Field of Classification Search
CPC ..... A61M 5/14; A61M 5/142; A61M 5/1422; A61M 5/14224; A61M 5/14228; A61M 5/145; A61M 5/1452; A61M 5/14526; A61M 5/148; A61M 5/152; A61M 5/141; A61M 2005/14506; A61M 2005/14513; A61M 2001/1032; A61M 1/106; F04B 9/1095; F04B 11/0075; F04B 15/02; F04B 9/1178
USPC ........ 604/131, 151, 891.1, 133, 81, 191, 258, 604/284; 417/385, 390
See application file for complete search history.

(56) References Cited

U.S. PATENT DOCUMENTS 2,828,743 A 4/1858 Ashkenaz et al.
2,605,765 A 8/1952 Kollsman
(Continued)

FOREIGN PATENT DOCUMENTS

DE 3634725 A1 * 4/1988
DE 3739657 A1 5/1988
(Continued)

OTHER PUBLICATIONS

Third Official Examiner's Report for Australian patent application No. 2009202856 dated Dec. 6, 2011.
(Continued)

*Primary Examiner* — Andrew Gilbert
(74) *Attorney, Agent, or Firm* — Morgan, Lewis & Bockius LLP

(57) ABSTRACT

A fluid delivery device comprises a hydraulic pump chamber having a hydraulic fluid. A fluid reservoir is coupled to the hydraulic pump chamber and is configured to contain a fluid deliverable to a patient. A first actuator is coupled to the hydraulic pump chamber and is configured to pressurize the hydraulic pump chamber and configured to transfer energy through the hydraulic pump chamber to the fluid reservoir. A second actuator is coupled to the hydraulic pump chamber and is configured to pressurize the hydraulic pump chamber and configured to transfer energy through the hydraulic pump chamber to the fluid reservoir.

17 Claims, 8 Drawing Sheets

(51) Int. Cl.
*A61M 1/10* (2006.01)
*A61M 5/155* (2006.01)
*F04B 9/109* (2006.01)
*F04B 15/02* (2006.01)
*A61M 5/142* (2006.01)

(52) U.S. Cl.
CPC ....... *A61M37/0015* (2013.01); *A61M 5/14593* (2013.01); *A61M 2005/14264* (2013.01); *A61M 2005/14506* (2013.01); *A61M 2005/14513* (2013.01); *A61M 2037/0023* (2013.01); *A61M 2037/0038* (2013.01); *A61M 2037/0046* (2013.01); *F04B 9/1095* (2013.01); *F04B 15/02* (2013.01)

(56) References Cited

U.S. PATENT DOCUMENTS

| | | |
|---|---|---|
| 2,702,547 A | 2/1955 | Glass |
| 3,055,362 A | 9/1962 | Uytenbogaart |
| 3,187,749 A | 6/1965 | Sarnoff |
| 3,731,681 A | 5/1973 | Blackshear et al. |
| 3,886,938 A | 6/1975 | Szabo et al. |
| 3,963,151 A | 6/1976 | North, Jr. |
| 4,042,153 A | 8/1977 | Callahan et al. |
| 4,065,230 A | 12/1977 | Gezari |
| 4,085,749 A | 4/1978 | Chambron |
| 4,150,672 A | 4/1979 | Whitney et al. |
| 4,190,048 A | 2/1980 | Sampson |
| 4,193,397 A | 3/1980 | Tucker et al. |
| 4,202,333 A | 5/1980 | Thill et al. |
| 4,209,014 A | 6/1980 | Sefton |
| 4,258,711 A | 3/1981 | Tucker et al. |
| 4,267,836 A | 5/1981 | Whitney et al. |
| 4,298,000 A | 11/1981 | Thill et al. |
| 4,313,439 A | 2/1982 | Babb et al. |
| 4,340,048 A | 7/1982 | Eckenhoff |
| 4,351,335 A | 9/1982 | Whitney et al. |
| 4,360,019 A | 11/1982 | Portner et al. |
| 4,398,908 A | 8/1983 | Siposs |
| 4,411,651 A | 10/1983 | Schulman |
| 4,430,079 A | 2/1984 | Thill et al. |
| 4,431,426 A | 2/1984 | Groshong et al. |
| 4,437,859 A * | 3/1984 | Whitehouse et al. .......... 604/131 |
| 4,443,218 A | 4/1984 | DeCant, Jr. et al. |
| 4,470,771 A * | 9/1984 | Hall et al. ...................... 417/342 |
| 4,490,096 A * | 12/1984 | Box ................................. 417/342 |
| 4,496,343 A | 1/1985 | Prosl et al. |
| 4,498,843 A | 2/1985 | Schneider et al. |
| 4,525,165 A | 6/1985 | Fischell |
| 4,529,401 A | 7/1985 | Leslie et al. |
| 4,548,607 A | 10/1985 | Harris |
| 4,552,561 A | 11/1985 | Eckenhoff et al. |
| 4,559,038 A | 12/1985 | Berg et al. |
| 4,561,856 A | 12/1985 | Cochran |
| 4,565,542 A | 1/1986 | Berg |
| 4,568,335 A | 2/1986 | Updike et al. |
| 4,583,973 A | 4/1986 | Humphrey et al. |
| 4,596,575 A | 6/1986 | Rosenberg et al. |
| 4,601,707 A | 7/1986 | Albisser et al. |
| H150 H | 11/1986 | Hankner et al. |
| 4,627,839 A | 12/1986 | Young |
| 4,648,872 A | 3/1987 | Kamen |
| 4,650,469 A | 3/1987 | Berg et al. |
| 4,685,902 A | 8/1987 | Edwards et al. |
| 4,699,615 A | 10/1987 | Fischell et al. |
| 4,715,852 A | 12/1987 | Reinicke et al. |
| 4,718,893 A | 1/1988 | Dorman et al. |
| 4,723,947 A | 2/1988 | Konopka |
| 4,731,058 A | 3/1988 | Doan |
| 4,734,092 A | 3/1988 | Millerd |
| 4,741,736 A | 5/1988 | Brown |
| 4,744,786 A | 5/1988 | Hooven |
| 4,747,824 A | 5/1988 | Spinello |
| 4,749,109 A | 6/1988 | Kamen |
| 4,755,172 A | 7/1988 | Baldwin |
| 4,772,263 A | 9/1988 | Dorman et al. |
| 4,772,273 A | 9/1988 | Alchas |
| 4,781,688 A | 11/1988 | Thoma et al. |
| 4,784,576 A | 11/1988 | Bloom et al. |
| 4,784,577 A | 11/1988 | Ritson et al. |
| 4,790,829 A | 12/1988 | Bowden et al. |
| 4,808,161 A | 2/1989 | Kamen |
| 4,808,167 A | 2/1989 | Mann et al. |
| 4,813,951 A | 3/1989 | Cannon et al. |
| 4,816,019 A | 3/1989 | Kamen |
| 4,818,186 A | 4/1989 | Pastrone et al. |
| 4,822,339 A | 4/1989 | Tran |
| 4,826,482 A | 5/1989 | Kamen |
| 4,834,704 A | 5/1989 | Reinicke |
| 4,838,857 A | 6/1989 | Strowe et al. |
| 4,842,584 A | 6/1989 | Pastrone |
| 4,846,806 A | 7/1989 | Wigness et al. |
| 4,856,340 A | 8/1989 | Garrison |
| 4,861,341 A | 8/1989 | Woodburn |
| 4,874,386 A | 10/1989 | O'Boyle |
| 4,886,499 A | 12/1989 | Cirelli et al. |
| 4,894,054 A | 1/1990 | Miskinyar |
| 4,900,305 A | 2/1990 | Smith et al. |
| 4,902,278 A | 2/1990 | Maget et al. |
| 4,919,134 A | 4/1990 | Streeter |
| 4,925,444 A | 5/1990 | Orkin et al. |
| 4,927,411 A | 5/1990 | Pastrone et al. |
| 4,931,050 A | 6/1990 | Idriss |
| 4,952,210 A | 8/1990 | Alchas |
| 4,971,900 A | 11/1990 | Ahnell et al. |
| 4,976,162 A | 12/1990 | Kamen |
| 4,976,696 A | 12/1990 | Sanderson et al. |
| 4,998,926 A | 3/1991 | Alchas |
| 5,000,994 A | 3/1991 | Romberg et al. |
| 5,009,641 A | 4/1991 | Gorton |
| 5,024,664 A | 6/1991 | Mitchell |
| 5,037,396 A | 8/1991 | Streeter |
| 5,039,279 A | 8/1991 | Natwick et al. |
| 5,041,094 A | 8/1991 | Perego et al. |
| 5,045,064 A | 9/1991 | Idriss |
| 5,053,031 A | 10/1991 | Borsanyi |
| 5,055,001 A | 10/1991 | Natwick et al. |
| 5,059,174 A | 10/1991 | Vaillancourt |
| 5,062,774 A | 11/1991 | Kramer et al. |
| 5,088,515 A | 2/1992 | Kamen |
| 5,090,963 A | 2/1992 | Gross et al. |
| 5,098,262 A | 3/1992 | Wecker et al. |
| 5,100,380 A | 3/1992 | Epstein et al. |
| 5,106,374 A | 4/1992 | Apperson et al. |
| 5,106,627 A | 4/1992 | Aebischer et al. |
| 5,108,367 A | 4/1992 | Epstein et al. |
| 5,135,498 A | 8/1992 | Kam et al. |
| 5,135,500 A | 8/1992 | Zdeb |
| 5,144,515 A | 9/1992 | Frauhauf et al. |
| 5,158,437 A | 10/1992 | Natwick et al. |
| 5,165,869 A * | 11/1992 | Reynolds ...................... 417/385 |
| 5,167,631 A | 12/1992 | Thompson et al. |
| 5,169,390 A | 12/1992 | Athayde et al. |
| 5,176,502 A | 1/1993 | Sanderson et al. |
| 5,176,641 A | 1/1993 | Idriss |
| 5,176,644 A | 1/1993 | Srisathapat et al. |
| 5,178,182 A | 1/1993 | Kamen |
| 5,178,609 A | 1/1993 | Ishikawa |
| 5,180,287 A | 1/1993 | Natwick et al. |
| 5,181,910 A | 1/1993 | Scanlon |
| 5,188,603 A | 2/1993 | Vaillancourt |
| 5,193,990 A | 3/1993 | Kamen et al. |
| 5,197,322 A | 3/1993 | Indravudh |
| 5,207,642 A | 5/1993 | Orkin et al. |
| 5,207,666 A | 5/1993 | Idriss et al. |
| 5,211,201 A | 5/1993 | Kamen et al. |
| 5,217,442 A | 6/1993 | Davis |
| 5,219,279 A | 6/1993 | Natwick et al. |
| 5,219,428 A | 6/1993 | Stern |
| 5,222,946 A | 6/1993 | Kamen |
| 5,232,449 A | 8/1993 | Stern et al. |
| 5,242,408 A | 9/1993 | Jhuboo et al. |
| 5,248,300 A | 9/1993 | Bryant et al. |

(56) References Cited

U.S. PATENT DOCUMENTS

| | | | |
|---|---|---|---|
| 5,250,649 A | 10/1993 | Onwumere et al. |
| 5,254,096 A | 10/1993 | Rondelet et al. |
| 5,257,971 A | 11/1993 | Lord et al. |
| 5,257,987 A | 11/1993 | Athayde et al. |
| 5,259,732 A | 11/1993 | Stern |
| 5,261,884 A | 11/1993 | Stern et al. |
| 5,263,323 A | 11/1993 | Maus et al. |
| 5,281,210 A | 1/1994 | Burke et al. |
| 5,295,966 A | 3/1994 | Stern et al. |
| 5,295,967 A | 3/1994 | Rondelet et al. |
| 5,300,041 A | 4/1994 | Haber et al. |
| 5,304,126 A | 4/1994 | Epstein et al. |
| 5,306,257 A | 4/1994 | Zdeb |
| 5,308,334 A | 5/1994 | Sancoff |
| 5,312,364 A | 5/1994 | Jacobs et al. |
| 5,319,979 A | 6/1994 | Abrahamson |
| 5,320,600 A | 6/1994 | Lambert |
| 5,322,422 A | 6/1994 | Natwick et al. |
| 5,328,459 A | 7/1994 | Laghi |
| 5,338,157 A | 8/1994 | Blomquist |
| 5,338,312 A | 8/1994 | Montgomery |
| 5,349,852 A | 9/1994 | Kamen et al. |
| 5,350,357 A | 9/1994 | Kamen et al. |
| 5,356,379 A | 10/1994 | Vaillancourt |
| 5,364,242 A | 11/1994 | Olsen |
| 5,368,562 A | 11/1994 | Blomquist et al. |
| 5,368,571 A | 11/1994 | Horres, Jr. |
| 5,370,622 A | 12/1994 | Livingston et al. |
| 5,376,070 A | 12/1994 | Purvis et al. |
| 5,389,078 A | 2/1995 | Zalesky et al. |
| 2,703,084 A | 3/1995 | Tomlinson |
| 5,396,925 A | 3/1995 | Poli |
| 5,399,166 A | 3/1995 | Laing |
| 5,399,823 A | 3/1995 | McCusker |
| 5,405,614 A | 4/1995 | D'Angelo et al. |
| 5,421,823 A | 6/1995 | Kamen et al. |
| 5,431,626 A | 7/1995 | Bryant et al. |
| 5,431,634 A | 7/1995 | Brown |
| 5,433,710 A | 7/1995 | Van Antwerp et al. |
| 5,438,510 A | 8/1995 | Bryant et al. |
| 5,445,621 A | 8/1995 | Poli et al. |
| 5,447,286 A | 9/1995 | Kamen et al. |
| 5,453,099 A | 9/1995 | Lee et al. |
| 5,456,909 A | 10/1995 | Marsh, Jr. et al. |
| 5,456,940 A | 10/1995 | Funderburk |
| 5,460,618 A | 10/1995 | Harreld |
| 5,462,525 A | 10/1995 | Srisathapat et al. |
| 5,464,392 A | 11/1995 | Epstein et al. |
| 5,466,218 A | 11/1995 | Srisathapat et al. |
| 5,472,317 A | 12/1995 | Field et al. |
| 5,474,683 A | 12/1995 | Bryant et al. |
| 5,480,386 A | 1/1996 | Brohy et al. |
| 5,485,408 A | 1/1996 | Blomquist |
| 5,487,737 A | 1/1996 | Meyer et al. |
| 5,492,534 A * | 2/1996 | Athayde et al. ............... 604/141 |
| 5,505,706 A | 4/1996 | Maus et al. |
| 5,505,709 A | 4/1996 | Funderburk et al. |
| 5,505,713 A | 4/1996 | Van Antwerp |
| 5,507,277 A | 4/1996 | Rubsamen et al. |
| 5,514,103 A | 5/1996 | Srisathapat et al. |
| 5,515,713 A | 5/1996 | Saugues et al. |
| 5,526,844 A | 6/1996 | Kamen et al. |
| 5,527,288 A | 6/1996 | Gross et al. |
| 5,527,307 A | 6/1996 | Srisathapat et al. |
| 5,529,463 A | 6/1996 | Layer et al. |
| 5,531,697 A | 7/1996 | Olsen et al. |
| 5,531,698 A | 7/1996 | Olsen |
| 5,533,389 A | 7/1996 | Kamen et al. |
| 5,533,994 A | 7/1996 | Meyer et al. |
| 5,538,399 A | 7/1996 | Johnson |
| 5,538,511 A | 7/1996 | Van Antwerp |
| 5,540,561 A | 7/1996 | Johnson |
| 5,544,519 A | 8/1996 | Hammarberg et al. |
| 5,545,152 A | 8/1996 | Funderburk et al. |
| 5,564,915 A | 10/1996 | Johnson |
| 5,567,119 A | 10/1996 | Johnson |
| 5,567,136 A | 10/1996 | Johnson |
| 5,569,186 A | 10/1996 | Lord et al. |
| 5,570,716 A | 11/1996 | Kamen et al. |
| 5,574,008 A | 11/1996 | Johnson et al. |
| 5,575,310 A | 11/1996 | Kamen et al. |
| 5,575,770 A | 11/1996 | Melsky et al. |
| 5,578,002 A | 11/1996 | Slettenmark et al. |
| 5,578,005 A | 11/1996 | Sancoff et al. |
| 5,578,012 A | 11/1996 | Kamen et al. |
| 5,582,591 A | 12/1996 | Cheikh et al. |
| 5,584,813 A | 12/1996 | Livingston et al. |
| 5,584,815 A | 12/1996 | Pawelka et al. |
| 5,602,171 A | 2/1997 | Tang et al. |
| 5,607,418 A | 3/1997 | Arzbaecher |
| 5,614,642 A | 3/1997 | Tang et al. |
| 5,616,123 A | 4/1997 | Cheikh et al. |
| 5,628,908 A | 5/1997 | Kamen et al. |
| 5,634,779 A * | 6/1997 | Eysymontt ............... 417/342 |
| 5,634,896 A | 6/1997 | Bryant et al. |
| 5,635,387 A | 6/1997 | Fei et al. |
| 5,637,095 A | 6/1997 | Nason et al. |
| 5,637,099 A | 6/1997 | Durdin et al. |
| 5,641,892 A | 6/1997 | Larkins et al. |
| 5,647,853 A | 7/1997 | Feldmann et al. |
| 5,647,854 A | 7/1997 | Olsen et al. |
| 5,655,897 A | 8/1997 | Neftel et al. |
| 5,656,032 A | 8/1997 | Kriesel et al. |
| 5,658,250 A | 8/1997 | Blomquist et al. |
| 5,658,252 A | 8/1997 | Johnson |
| 5,660,846 A | 8/1997 | Cheikh et al. |
| 5,665,065 A | 9/1997 | Colman et al. |
| 5,665,070 A | 9/1997 | McPhee |
| 5,669,877 A | 9/1997 | Blomquist |
| 5,672,167 A | 9/1997 | Athayde et al. |
| 5,693,018 A | 12/1997 | Kriesel et al. |
| 5,694,919 A | 12/1997 | Rubsamen et al. |
| 5,695,473 A | 12/1997 | Olsen |
| 5,700,244 A | 12/1997 | Kriesel |
| 5,700,904 A | 12/1997 | Baker et al. |
| 5,702,372 A | 12/1997 | Nelson |
| 5,707,361 A | 1/1998 | Slettenmark et al. |
| 5,713,865 A | 2/1998 | Manning et al. |
| 5,716,343 A * | 2/1998 | Kriesel et al. ............... 604/132 |
| 5,718,568 A | 2/1998 | Neftel et al. |
| 5,722,397 A | 3/1998 | Eppstein |
| 5,722,956 A | 3/1998 | Sims et al. |
| 5,735,263 A | 4/1998 | Rubsamen et al. |
| 5,738,658 A | 4/1998 | Maus et al. |
| 5,741,125 A | 4/1998 | Neftel et al. |
| 5,749,835 A | 5/1998 | Glantz |
| 5,755,683 A | 5/1998 | Houle et al. |
| 5,764,159 A | 6/1998 | Neftel et al. |
| 5,772,409 A | 6/1998 | Johnson |
| 5,776,103 A | 7/1998 | Kriesel et al. |
| 5,777,060 A | 7/1998 | Van Antwerp |
| 5,782,798 A | 7/1998 | Rise |
| 5,785,681 A | 7/1998 | Indravudh |
| 5,785,688 A | 7/1998 | Joshi et al. |
| 5,788,671 A | 8/1998 | Johnson |
| 5,788,673 A | 8/1998 | Young et al. |
| 5,788,678 A | 8/1998 | Van Antwerp |
| 5,792,123 A | 8/1998 | Ensminger |
| 5,800,420 A | 9/1998 | Gross et al. |
| 5,800,421 A | 9/1998 | Lemelson |
| 5,807,315 A | 9/1998 | Van Antwerp et al. |
| 5,807,375 A | 9/1998 | Gross et al. |
| 5,810,771 A | 9/1998 | Blomquist |
| 5,820,622 A | 10/1998 | Gross et al. |
| 5,823,746 A | 10/1998 | Johnson |
| 5,827,262 A | 10/1998 | Neftel et al. |
| 5,837,234 A | 11/1998 | Gentile et al. |
| 5,837,276 A | 11/1998 | Cheikh et al. |
| 5,837,680 A | 11/1998 | Moses et al. |
| 5,843,023 A | 12/1998 | Cecchi |
| 5,848,990 A | 12/1998 | Cirelli et al. |
| 5,851,197 A | 12/1998 | Marano et al. |
| 5,858,969 A | 1/1999 | Marsh, Jr. et al. |
| 5,868,711 A | 2/1999 | Kramer et al. |

(56) References Cited

U.S. PATENT DOCUMENTS

| | | | |
|---|---|---|---|
| 5,873,857 A | 2/1999 | Kriesel |
| 5,876,370 A | 3/1999 | Blomquist |
| 5,879,143 A | 3/1999 | Cote et al. |
| 5,882,494 A | 3/1999 | Van Antwerp |
| 5,891,086 A | 4/1999 | Weston |
| 5,906,592 A | 5/1999 | Kriesel et al. |
| 5,921,962 A | 7/1999 | Kriesel et al. |
| 5,928,196 A | 7/1999 | Johnson et al. |
| 5,935,099 A | 8/1999 | Peterson et al. |
| 5,935,105 A | 8/1999 | Manning et al. |
| 5,935,106 A | 8/1999 | Olsen |
| 5,935,598 A | 8/1999 | Sage et al. |
| 5,944,695 A | 8/1999 | Johnson et al. |
| 5,951,521 A | 9/1999 | Mastrototaro et al. |
| 5,952,347 A | 9/1999 | Arison et al. |
| 5,954,485 A | 9/1999 | Johnson et al. |
| 5,954,695 A | 9/1999 | Sims et al. |
| 5,957,890 A | 9/1999 | Mann et al. |
| 5,957,895 A | 9/1999 | Sage et al. |
| 5,960,797 A | 10/1999 | Kramer et al. |
| 5,961,499 A | 10/1999 | Bonutti et al. |
| 5,968,014 A | 10/1999 | Neftel et al. |
| 5,976,109 A * | 11/1999 | Heruth ............................ 604/140 |
| 5,989,423 A | 11/1999 | Kamen et al. |
| 5,995,860 A | 11/1999 | Sun et al. |
| 6,002,954 A | 12/1999 | Van Antwerp et al. |
| 6,006,753 A | 12/1999 | Efendic |
| 6,007,555 A | 12/1999 | Devine |
| 6,011,984 A | 1/2000 | Van Antwerp et al. |
| 6,012,034 A | 1/2000 | Hamparian et al. |
| 6,013,057 A | 1/2000 | Danby et al. |
| 6,017,318 A | 1/2000 | Gauthier et al. |
| 6,022,316 A | 2/2000 | Eppstein et al. |
| 6,024,539 A | 2/2000 | Blomquist |
| 6,025,331 A | 2/2000 | Moses et al. |
| 6,030,399 A | 2/2000 | Ignotz et al. |
| 6,040,194 A | 3/2000 | Chick et al. |
| 6,041,801 A | 3/2000 | Gray et al. |
| 6,043,273 A | 3/2000 | Duhaylongsod |
| 6,045,734 A | 4/2000 | Luther et al. |
| 6,048,328 A | 4/2000 | Haller et al. |
| 6,049,727 A | 4/2000 | Crothall |
| 6,051,557 A | 4/2000 | Drucker |
| 6,053,893 A | 4/2000 | Bucher et al. |
| 6,056,718 A | 5/2000 | Funderburk et al. |
| 6,056,734 A | 5/2000 | Jacobsen et al. |
| 6,057,131 A | 5/2000 | Marsh, Jr. et al. |
| 6,059,753 A | 5/2000 | Faust et al. |
| 6,065,941 A | 5/2000 | Gray et al. |
| 6,070,761 A | 6/2000 | Bloom et al. |
| 6,074,369 A | 6/2000 | Sage et al. |
| 6,077,055 A | 6/2000 | Vilks |
| 6,077,246 A | 6/2000 | Kullas et al. |
| 6,077,248 A | 6/2000 | Zumschlinge et al. |
| 6,077,259 A | 6/2000 | Caizza et al. |
| 6,083,201 A | 7/2000 | Skinkle |
| 6,085,574 A | 7/2000 | Neftel et al. |
| 6,087,394 A | 7/2000 | Duhaylongsod |
| 6,092,249 A | 7/2000 | Kamen et al. |
| 6,093,167 A | 7/2000 | Houben et al. |
| 6,093,172 A | 7/2000 | Funderburk et al. |
| 6,105,829 A * | 8/2000 | Snodgrass et al. ............ 222/214 |
| 6,110,152 A | 8/2000 | Kovelman |
| 6,110,427 A | 8/2000 | Uffenheimer |
| 6,110,721 A | 8/2000 | Gibbs et al. |
| 6,112,111 A | 8/2000 | Glantz |
| RE36,871 E | 9/2000 | Epstein et al. |
| 6,120,460 A | 9/2000 | Abreu |
| 6,122,536 A | 9/2000 | Sun et al. |
| 6,123,668 A | 9/2000 | Abreu |
| 6,123,685 A | 9/2000 | Reynolds |
| 6,123,686 A | 9/2000 | Olsen et al. |
| 6,126,642 A | 10/2000 | Kriesel et al. |
| 6,127,410 A | 10/2000 | Duhaylongsod |
| 6,135,978 A | 10/2000 | Houben et al. |
| D434,142 S | 11/2000 | Cheney, II et al. |
| 6,142,939 A | 11/2000 | Eppstein et al. |
| 6,142,972 A | 11/2000 | Cheikh et al. |
| 6,152,898 A | 11/2000 | Olsen et al. |
| 6,155,824 A | 12/2000 | Kamen et al. |
| 6,165,154 A | 12/2000 | Gray et al. |
| 6,168,609 B1 | 1/2001 | Kamen et al. |
| 6,175,752 B1 | 1/2001 | Say et al. |
| 6,183,434 B1 | 2/2001 | Eppstein |
| 6,183,441 B1 | 2/2001 | Kriesel et al. |
| 6,186,982 B1 | 2/2001 | Gross et al. |
| 6,190,359 B1 | 2/2001 | Heruth |
| 6,191,102 B1 | 2/2001 | DiMarchi et al. |
| 6,193,704 B1 | 2/2001 | Winters |
| 6,202,708 B1 | 3/2001 | Bynum |
| 6,203,528 B1 | 3/2001 | Deckert et al. |
| 6,206,850 B1 | 3/2001 | O'Neil et al. |
| 6,207,856 B1 | 3/2001 | Veech |
| 6,210,361 B1 | 4/2001 | Kamen et al. |
| 6,213,943 B1 | 4/2001 | Abreu |
| 6,214,617 B1 | 4/2001 | Herman |
| 6,223,130 B1 | 4/2001 | Gray et al. |
| 6,228,060 B1 | 5/2001 | Howell |
| 6,231,320 B1 | 5/2001 | Lawless et al. |
| 6,231,545 B1 | 5/2001 | Kriesel et al. |
| 6,234,997 B1 | 5/2001 | Kamen et al. |
| 6,241,704 B1 | 6/2001 | Peterson et al. |
| 6,248,067 B1 | 6/2001 | Causey, III et al. |
| 6,248,093 B1 | 6/2001 | Moberg |
| 6,251,098 B1 | 6/2001 | Rake et al. |
| 6,253,804 B1 | 7/2001 | Safabash |
| 6,254,586 B1 | 7/2001 | Mann et al. |
| 6,259,587 B1 | 7/2001 | Sheldon et al. |
| 6,261,272 B1 | 7/2001 | Gross et al. |
| 6,261,280 B1 | 7/2001 | Houben et al. |
| 6,267,564 B1 | 7/2001 | Rapheal |
| D446,854 S | 8/2001 | Cheney, II et al. |
| 6,270,478 B1 | 8/2001 | MemØe |
| 6,283,943 B1 | 9/2001 | Dy et al. |
| 6,284,725 B1 | 9/2001 | Coolidge et al. |
| 6,284,727 B1 | 9/2001 | Kim et al. |
| 6,287,294 B1 | 9/2001 | Lemelson |
| 6,287,521 B1 | 9/2001 | Quay et al. |
| 6,293,925 B1 | 9/2001 | Safabash et al. |
| 6,302,653 B1 | 10/2001 | Bryant et al. |
| 6,302,990 B1 | 10/2001 | Nelson |
| 6,306,420 B1 | 10/2001 | Cheikh et al. |
| 6,312,393 B1 | 11/2001 | Abreu |
| 6,315,769 B1 | 11/2001 | Peer et al. |
| 6,316,038 B1 | 11/2001 | Veech |
| 6,319,540 B1 | 11/2001 | Van Antwerp et al. |
| 6,321,597 B1 | 11/2001 | Demers et al. |
| 6,323,237 B1 | 11/2001 | Veech |
| 6,329,336 B1 | 12/2001 | Bridon et al. |
| 6,334,856 B1 | 1/2002 | Allen et al. |
| 6,338,730 B1 | 1/2002 | Bonutti et al. |
| D453,830 S | 2/2002 | McDowell et al. |
| 6,343,614 B1 | 2/2002 | Gray et al. |
| 6,346,095 B1 | 2/2002 | Gross et al. |
| 6,348,043 B1 * | 2/2002 | Hagen et al. .................. 604/151 |
| 6,355,019 B1 | 3/2002 | Kriesel et al. |
| 6,355,021 B1 | 3/2002 | Nielsen et al. |
| 6,360,888 B1 | 3/2002 | McIvor et al. |
| 6,362,591 B1 | 3/2002 | Moberg |
| 6,364,279 B1 | 4/2002 | Neftel et al. |
| 6,364,857 B1 | 4/2002 | Gray et al. |
| 6,368,274 B1 | 4/2002 | Van Antwerp et al. |
| 6,374,876 B2 | 4/2002 | Bynum |
| 6,375,459 B1 | 4/2002 | Kamen et al. |
| 6,375,638 B2 | 4/2002 | Nason et al. |
| 6,379,345 B1 | 4/2002 | Constantz |
| 6,382,923 B1 | 5/2002 | Gray |
| 6,394,981 B2 | 5/2002 | Heruth |
| 6,403,558 B1 | 6/2002 | Moses et al. |
| 6,406,455 B1 | 6/2002 | Willis et al. |
| 6,414,018 B1 | 7/2002 | Duhaylongsod |
| 6,416,293 B1 | 7/2002 | Bouchard et al. |
| 6,416,495 B1 | 7/2002 | Kriesel et al. |
| 6,416,496 B1 | 7/2002 | Rogers et al. |

(56) References Cited

U.S. PATENT DOCUMENTS

| | | | |
|---|---|---|---|
| 6,422,057 B1 | 7/2002 | Anderson |
| 6,423,001 B1 | 7/2002 | Abreu |
| 6,423,035 B1 | 7/2002 | Das et al. |
| 6,424,847 B1 | 7/2002 | Mastrototaro et al. |
| 6,427,088 B1 | 7/2002 | Bowman, IV et al. |
| D461,241 S | 8/2002 | Moberg et al. |
| D461,891 S | 8/2002 | Moberg |
| 6,429,197 B1 | 8/2002 | Coolidge et al. |
| 6,432,383 B1 | 8/2002 | Modi |
| 6,436,072 B1 | 8/2002 | Kullas et al. |
| 6,440,933 B1 | 8/2002 | Bodor et al. |
| 6,443,942 B2 | 9/2002 | Van Antwerp et al. |
| 6,453,956 B2 | 9/2002 | Safabash |
| 6,458,102 B1 | 10/2002 | Mann et al. |
| 6,458,355 B1 | 10/2002 | Hsei et al. |
| 6,461,329 B1 | 10/2002 | Van Antwerp et al. |
| 6,461,331 B1 | 10/2002 | Van Antwerp |
| 6,464,667 B1 | 10/2002 | Kamen et al. |
| 6,464,671 B1 | 10/2002 | Elver et al. |
| 6,465,431 B1 | 10/2002 | Thorn et al. |
| 6,468,532 B1 | 10/2002 | Hsei et al. |
| 6,471,436 B1 | 10/2002 | Gjata et al. |
| 6,471,674 B1 | 10/2002 | Emig et al. |
| 6,475,180 B2 | 11/2002 | Peterson et al. |
| 6,475,196 B1 | 11/2002 | Vachon |
| 6,485,263 B1 | 11/2002 | Bryant et al. |
| 6,485,461 B1 | 11/2002 | Mason et al. |
| 6,485,465 B2 | 11/2002 | Moberg et al. |
| 6,495,366 B1 | 12/2002 | Briggs |
| 6,495,532 B1 | 12/2002 | Bathurst et al. |
| 6,500,150 B1 | 12/2002 | Gross et al. |
| 6,503,062 B1 | 1/2003 | Gray et al. |
| 6,503,184 B1 | 1/2003 | Ni et al. |
| 6,503,231 B1 | 1/2003 | Prausnitz et al. |
| 6,505,059 B1 | 1/2003 | Kollias et al. |
| 6,512,939 B1 | 1/2003 | Colvin et al. |
| 6,514,500 B1 | 2/2003 | Bridon et al. |
| 6,520,326 B2 | 2/2003 | McIvor et al. |
| 6,520,747 B2 | 2/2003 | Gray et al. |
| 6,520,936 B1 | 2/2003 | Mann |
| 6,520,938 B1 | 2/2003 | Funderburk et al. |
| D471,352 S | 3/2003 | Shetler et al. |
| 6,527,716 B1 * | 3/2003 | Eppstein ................ 600/309 |
| 6,530,900 B1 | 3/2003 | Dailey et al. |
| 6,537,268 B1 | 3/2003 | Gibson et al. |
| 6,544,193 B2 | 4/2003 | Abreu |
| 6,544,229 B1 | 4/2003 | Danby et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,555,986 B2 | 4/2003 | Moberg |
| 6,558,320 B1 | 5/2003 | Causey, III et al. |
| 6,558,343 B1 | 5/2003 | Neftel et al. |
| 6,558,345 B1 | 5/2003 | Houben et al. |
| 6,558,351 B1 | 5/2003 | Steil et al. |
| 6,560,471 B1 | 5/2003 | Heller et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,565,531 B1 | 5/2003 | Mori et al. |
| 6,565,534 B1 | 5/2003 | Winters |
| 6,565,535 B2 | 5/2003 | Zaias et al. |
| 6,565,885 B1 | 5/2003 | Tarara et al. |
| 6,571,128 B2 | 5/2003 | Lebel et al. |
| 6,572,586 B1 | 6/2003 | Wojcik |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,585,695 B1 | 7/2003 | Adair et al. |
| 6,586,401 B1 | 7/2003 | Thorn et al. |
| 6,589,229 B1 | 7/2003 | Connelly et al. |
| 6,589,936 B1 | 7/2003 | Thorn et al. |
| 6,591,876 B2 | 7/2003 | Safabash |
| 6,593,295 B2 | 7/2003 | Bridon et al. |
| 6,595,202 B2 | 7/2003 | Ganan-Calvo et al. |
| 6,595,756 B2 | 7/2003 | Gray et al. |
| 6,595,956 B1 | 7/2003 | Gross et al. |
| 6,604,908 B1 | 8/2003 | Bryant et al. |
| 6,607,509 B2 | 8/2003 | Bobroff et al. |
| 6,608,101 B1 | 8/2003 | Ni et al. |
| 6,609,898 B1 * | 8/2003 | Bury ........................ 417/347 |
| 6,610,288 B1 | 8/2003 | Edge et al. |
| 6,611,707 B1 | 8/2003 | Prausnitz et al. |
| 6,613,026 B1 | 9/2003 | Palasis et al. |
| 6,613,038 B2 | 9/2003 | Bonutti et al. |
| 6,616,627 B2 | 9/2003 | Willis et al. |
| 6,617,450 B1 | 9/2003 | Stocker et al. |
| 6,622,732 B2 | 9/2003 | Constantz |
| 6,629,954 B1 * | 10/2003 | Heruth ...................... 604/131 |
| 6,632,215 B1 | 10/2003 | Lemelson |
| 6,635,049 B1 | 10/2003 | Robinson et al. |
| 6,635,743 B1 | 10/2003 | Ebner et al. |
| 6,641,533 B2 | 11/2003 | Causey, III et al. |
| 6,641,562 B1 | 11/2003 | Peterson |
| 6,642,015 B2 | 11/2003 | Vachon et al. |
| 6,645,175 B1 | 11/2003 | Kriesel et al. |
| 6,648,821 B2 | 11/2003 | Lebel et al. |
| 6,651,656 B2 | 11/2003 | Demers et al. |
| 6,652,493 B1 | 11/2003 | Das |
| 6,652,510 B2 | 11/2003 | Lord et al. |
| 6,653,283 B1 | 11/2003 | Moses et al. |
| 6,656,148 B2 | 12/2003 | Das et al. |
| 6,656,158 B2 | 12/2003 | Gregory et al. |
| 6,656,159 B2 | 12/2003 | Flaherty |
| 6,659,948 B2 | 12/2003 | Lebel et al. |
| 6,659,982 B2 | 12/2003 | Douglas et al. |
| 6,660,509 B1 | 12/2003 | Herman et al. |
| 6,663,359 B2 | 12/2003 | Gray |
| 6,665,909 B2 | 12/2003 | Collins et al. |
| 6,666,845 B2 | 12/2003 | Hooper et al. |
| 6,669,663 B1 | 12/2003 | Thompson |
| 6,669,668 B1 | 12/2003 | Kleeman et al. |
| 6,669,669 B2 | 12/2003 | Flaherty et al. |
| 6,671,554 B2 | 12/2003 | Gibson et al. |
| 6,685,664 B2 | 2/2004 | Levin et al. |
| 6,687,546 B2 | 2/2004 | Lebel et al. |
| 6,689,073 B2 | 2/2004 | Quay |
| 6,689,100 B2 | 2/2004 | Connelly et al. |
| 6,689,108 B2 | 2/2004 | Lavi et al. |
| 6,689,607 B2 | 2/2004 | Ni et al. |
| 6,689,747 B2 | 2/2004 | Filvaroff et al. |
| 6,692,456 B1 | 2/2004 | Eppstein et al. |
| 6,692,457 B2 | 2/2004 | Flaherty |
| 6,694,191 B2 | 2/2004 | Starkweather et al. |
| 6,699,219 B2 | 3/2004 | Emig et al. |
| 6,702,779 B2 | 3/2004 | Connelly et al. |
| 6,703,217 B2 | 3/2004 | Herman et al. |
| 6,709,417 B1 | 3/2004 | Houle et al. |
| 6,711,436 B1 | 3/2004 | Duhaylongsod |
| 6,712,587 B2 * | 3/2004 | Gerhardt et al. .............. 417/390 |
| 6,716,190 B1 | 4/2004 | Glines et al. |
| 6,716,193 B1 | 4/2004 | Neftel |
| 6,721,582 B2 | 4/2004 | Trepagnier et al. |
| 6,723,072 B2 | 4/2004 | Faherty et al. |
| 6,726,656 B2 | 4/2004 | Kamen et al. |
| 6,728,560 B2 | 4/2004 | Kollias et al. |
| 6,733,446 B2 | 5/2004 | Lebel et al. |
| 6,734,162 B2 | 5/2004 | Van Antwerp et al. |
| 6,734,186 B1 | 5/2004 | Maw et al. |
| 6,736,795 B2 | 5/2004 | Michel |
| 6,737,401 B2 | 5/2004 | Kim et al. |
| 6,740,059 B2 | 5/2004 | Flaherty |
| 6,740,072 B2 | 5/2004 | Starkweather et al. |
| 6,740,075 B2 | 5/2004 | Lebel et al. |
| 6,740,655 B2 | 5/2004 | Magee et al. |
| 6,749,403 B2 | 6/2004 | Bryant et al. |
| 6,749,587 B2 | 6/2004 | Flaherty |
| 6,750,311 B1 | 6/2004 | Van Antwerp et al. |
| 6,752,299 B2 | 6/2004 | Shetler et al. |
| 6,752,785 B2 | 6/2004 | Van Antwerp et al. |
| 6,752,787 B1 | 6/2004 | Causey, III et al. |
| 6,753,177 B1 | 6/2004 | Stocker et al. |
| 6,753,328 B2 | 6/2004 | Wands et al. |
| 6,755,811 B1 | 6/2004 | Constantz |

(56) References Cited

U.S. PATENT DOCUMENTS

| | | |
|---|---|---|
| 6,758,810 B2 | 7/2004 | Lebel et al. |
| 6,766,183 B2 | 7/2004 | Walsh et al. |
| 6,768,425 B2 | 7/2004 | Flaherty et al. |
| 6,770,067 B2 | 8/2004 | Lorenzen et al. |
| 6,770,729 B2 | 8/2004 | Van Antwerp |
| 6,774,120 B1 | 8/2004 | Ferber et al. |
| 6,784,274 B2 | 8/2004 | Van Antwerp et al. |
| 6,792,982 B2 | 9/2004 | Lincoln et al. |
| 6,796,956 B2 | 9/2004 | Hartlaub et al. |
| 6,796,957 B2 | 9/2004 | Carpenter et al. |
| 6,800,071 B1 | 10/2004 | McConnell et al. |
| 6,800,663 B2 | 10/2004 | Asgarzadeh et al. |
| 6,801,420 B2 | 10/2004 | Talbot et al. |
| 6,802,823 B2 * | 10/2004 | Mason ............... 604/141 |
| 6,804,544 B2 | 10/2004 | Van Antwerp et al. |
| 6,805,687 B2 | 10/2004 | Dextradeur et al. |
| 6,805,693 B2 | 10/2004 | Gray et al. |
| 6,808,369 B2 | 10/2004 | Gray et al. |
| 6,808,506 B2 | 10/2004 | Lastovich et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,715 B2 | 11/2004 | Bonutti et al. |
| 6,817,990 B2 | 11/2004 | Yap et al. |
| 6,821,949 B2 | 11/2004 | Bridon et al. |
| 6,824,529 B2 | 11/2004 | Gross et al. |
| 6,827,702 B2 | 12/2004 | Lebel et al. |
| 6,830,558 B2 | 12/2004 | Flaherty et al. |
| 6,830,564 B2 | 12/2004 | Gray |
| 6,840,922 B2 | 1/2005 | Nielsen et al. |
| 6,843,782 B2 | 1/2005 | Gross et al. |
| 6,849,718 B2 | 2/2005 | Kaelin, Jr. et al. |
| 6,849,719 B2 | 2/2005 | Shi et al. |
| 6,902,544 B2 | 6/2005 | Ludin et al. |
| 6,936,029 B2 | 8/2005 | Mann et al. |
| 6,939,324 B2 | 9/2005 | Gonnelli et al. |
| 6,960,184 B2 | 11/2005 | Willis et al. |
| 6,979,316 B1 | 12/2005 | Rubin et al. |
| 7,011,234 B2 | 3/2006 | Stradella |
| 7,014,625 B2 | 3/2006 | Bengtsson |
| 7,022,107 B1 | 4/2006 | Christensen et al. |
| 7,108,686 B2 | 9/2006 | Burke et al. |
| 7,150,409 B2 | 12/2006 | Gonnelli et al. |
| 7,204,823 B2 | 4/2007 | Estes et al. |
| 7,250,037 B2 | 7/2007 | Shermer et al. |
| 7,337,922 B2 | 3/2008 | Rake et al. |
| 7,367,968 B2 | 5/2008 | Rosenberg et al. |
| 7,481,792 B2 | 1/2009 | Gonnelli et al. |
| 7,530,968 B2 * | 5/2009 | Gonnelli ............... 604/132 |
| 7,534,226 B2 | 5/2009 | Mernoe et al. |
| 7,678,079 B2 | 3/2010 | Shermer et al. |
| 8,070,726 B2 * | 12/2011 | Gonnelli et al. ............... 604/132 |
| 2001/0005781 A1 | 6/2001 | Bergens et al. |
| 2001/0010238 A1 | 8/2001 | Bynum |
| 2001/0016710 A1 | 8/2001 | Nason et al. |
| 2001/0027287 A1 | 10/2001 | Shmulewitz et al. |
| 2001/0031944 A1 | 10/2001 | Peterson et al. |
| 2001/0037083 A1 | 11/2001 | Hartlaub et al. |
| 2001/0053891 A1 | 12/2001 | Ackley |
| 2001/0056259 A1 | 12/2001 | Skinkle et al. |
| 2002/0004015 A1 | 1/2002 | Carlisle et al. |
| 2002/0019612 A1 | 2/2002 | Watanabe et al. |
| 2002/0040208 A1 | 4/2002 | Flaherty et al. |
| 2002/0045867 A1 | 4/2002 | Nielsen et al. |
| 2002/0055460 A1 | 5/2002 | Coolidge et al. |
| 2002/0061838 A1 | 5/2002 | Holmquist et al. |
| 2002/0072733 A1 | 6/2002 | Flaherty |
| 2002/0077599 A1 | 6/2002 | Wojcik |
| 2002/0091358 A1 | 7/2002 | Klitmose |
| 2002/0095124 A1 | 7/2002 | Palasis et al. |
| 2002/0123716 A1 | 9/2002 | VanDiver et al. |
| 2002/0123735 A1 * | 9/2002 | Rake et al. ............... 604/407 |
| 2002/0123740 A1 | 9/2002 | Flaherty et al. |
| 2002/0128594 A1 | 9/2002 | Das et al. |
| 2002/0138049 A1 | 9/2002 | Allen et al. |
| 2002/0147131 A1 | 10/2002 | Coolidge et al. |
| 2002/0151842 A1 | 10/2002 | Gonnelli et al. |
| 2002/0151846 A1 | 10/2002 | Christenson et al. |
| 2002/0156418 A1 | 10/2002 | Gonnelli et al. |
| 2002/0156464 A1 | 10/2002 | Blischak et al. |
| 2002/0177809 A1 | 11/2002 | Kriesel et al. |
| 2002/0183693 A1 | 12/2002 | Peterson et al. |
| 2002/0188259 A1 | 12/2002 | Hickle et al. |
| 2002/0198493 A1 | 12/2002 | Diaz et al. |
| 2002/0198494 A1 | 12/2002 | Diaz et al. |
| 2003/0009133 A1 | 1/2003 | Ramey |
| 2003/0022823 A1 | 1/2003 | Efendic |
| 2003/0024508 A1 | 2/2003 | Heller et al. |
| 2003/0050237 A1 | 3/2003 | Kim et al. |
| 2003/0050623 A1 | 3/2003 | Lord et al. |
| 2003/0073626 A1 | 4/2003 | Hathaway et al. |
| 2003/0100888 A1 | 5/2003 | Spinello |
| 2003/0125669 A1 | 7/2003 | Safabash et al. |
| 2003/0130619 A1 | 7/2003 | Safabash et al. |
| 2003/0130647 A1 | 7/2003 | Gray et al. |
| 2003/0135158 A1 | 7/2003 | Gonnelli |
| 2003/0135160 A1 | 7/2003 | Gray et al. |
| 2003/0158520 A1 | 8/2003 | Safabash et al. |
| 2003/0163223 A1 | 8/2003 | Blomquist |
| 2003/0167039 A1 | 9/2003 | Moberg |
| 2003/0195157 A1 | 10/2003 | Natarajan et al. |
| 2003/0199445 A1 | 10/2003 | Knudsen et al. |
| 2003/0199823 A1 | 10/2003 | Bobroff et al. |
| 2003/0212000 A1 | 11/2003 | Van Antwerp |
| 2003/0216714 A1 | 11/2003 | Gill |
| 2003/0220610 A1 | 11/2003 | Lastovich et al. |
| 2003/0225373 A1 | 12/2003 | Bobroff et al. |
| 2003/0229309 A1 | 12/2003 | Babkes et al. |
| 2003/0233069 A1 | 12/2003 | Gillespie et al. |
| 2004/0002682 A1 | 1/2004 | Kovelman et al. |
| 2004/0029784 A1 | 2/2004 | Hathaway |
| 2004/0064086 A1 | 4/2004 | Gottlieb et al. |
| 2004/0064096 A1 | 4/2004 | Flaherty et al. |
| 2004/0064097 A1 | 4/2004 | Peterson |
| 2004/0073161 A1 | 4/2004 | Tachibana |
| 2004/0077000 A1 | 4/2004 | Stocker et al. |
| 2004/0085215 A1 | 5/2004 | Moberg et al. |
| 2004/0091374 A1 | 5/2004 | Gray |
| 2004/0092873 A1 | 5/2004 | Moberg |
| 2004/0092893 A1 | 5/2004 | Haider et al. |
| 2004/0094823 A1 | 5/2004 | Matsuno |
| 2004/0115067 A1 | 6/2004 | Rush et al. |
| 2004/0116905 A1 * | 6/2004 | Pedersen et al. ............ 604/890.1 |
| 2004/0126372 A1 | 7/2004 | Banerjee et al. |
| 2004/0126373 A1 | 7/2004 | Banerjee et al. |
| 2004/0133163 A1 | 7/2004 | Schiffmann |
| 2004/0143216 A1 | 7/2004 | Douglas et al. |
| 2004/0143217 A1 | 7/2004 | Michel |
| 2004/0143218 A1 | 7/2004 | Das |
| 2004/0153032 A1 | 8/2004 | Garribotto et al. |
| 2004/0155079 A1 | 8/2004 | Shetler et al. |
| 2004/0167464 A1 | 8/2004 | Ireland et al. |
| 2004/0167470 A1 | 8/2004 | Emig et al. |
| 2004/0176725 A1 | 9/2004 | Stutz et al. |
| 2004/0209801 A1 | 10/2004 | Brand et al. |
| 2004/0220456 A1 | 11/2004 | Eppstein |
| 2004/0220525 A1 | 11/2004 | Willis et al. |
| 2004/0225281 A1 | 11/2004 | Lorenzen et al. |
| 2004/0247445 A1 | 12/2004 | Nelson et al. |
| 2004/0249363 A1 | 12/2004 | Burke et al. |
| 2004/0250382 A1 | 12/2004 | Collins et al. |
| 2004/0254525 A1 | 12/2004 | Uber et al. |
| 2004/0260234 A1 | 12/2004 | Srinivasan et al. |
| 2004/0266678 A1 | 12/2004 | Beeley et al. |
| 2004/0267201 A1 | 12/2004 | Agerup |
| 2005/0008661 A1 | 1/2005 | Fereira et al. |
| 2005/0024175 A1 | 2/2005 | Gray et al. |
| 2005/0033232 A1 | 2/2005 | Kriesel |
| 2005/0054988 A1 | 3/2005 | Rosenberg et al. |
| 2005/0065472 A1 | 3/2005 | Cindrich et al. |
| 2005/0070875 A1 | 3/2005 | Kulessa |

(56) References Cited

U.S. PATENT DOCUMENTS

| | | |
|---|---|---|
| 2005/0112188 A1 | 5/2005 | Eliaz et al. |
| 2005/0137530 A1 | 6/2005 | Campbell et al. |
| 2005/0137578 A1 | 6/2005 | Heruth et al. |
| 2005/0171477 A1 | 8/2005 | Rubin et al. |
| 2005/0171512 A1 | 8/2005 | Flaherty |
| 2005/0177109 A1 | 8/2005 | Azzolini |
| 2005/0215850 A1 | 9/2005 | Klein et al. |
| 2005/0234428 A1 | 10/2005 | Spohn et al. |
| 2005/0245904 A1 | 11/2005 | Estes et al. |
| 2005/0273083 A1 | 12/2005 | Lebel et al. |
| 2005/0277912 A1* | 12/2005 | John .................... 604/890.1 |
| 2005/0278073 A1 | 12/2005 | Roth |
| 2006/0030838 A1 | 2/2006 | Gonnelli |
| 2006/0069382 A1 | 3/2006 | Pedersen |
| 2006/0079862 A1* | 4/2006 | Genosar ............... 604/890.1 |
| 2006/0100578 A1 | 5/2006 | Lieberman |
| 2006/0122628 A1 | 6/2006 | Solar et al. |
| 2006/0150747 A1 | 7/2006 | Mallett |
| 2006/0184119 A1 | 8/2006 | Remde et al. |
| 2006/0184154 A1 | 8/2006 | Moberg et al. |
| 2006/0189939 A1 | 8/2006 | Gonnelli et al. |
| 2006/0200112 A1 | 9/2006 | Paul |
| 2006/0264831 A1 | 11/2006 | Skwarek et al. |
| 2006/0264835 A1 | 11/2006 | Nielsen et al. |
| 2007/0016170 A1 | 1/2007 | Kovelman |
| 2007/0060894 A1 | 3/2007 | Dai et al. |
| 2007/0073236 A1 | 3/2007 | Mernoe et al. |
| 2007/0100283 A1 | 5/2007 | Causey, III et al. |
| 2007/0149925 A1 | 6/2007 | Edwards et al. |
| 2007/0167912 A1 | 7/2007 | Causey et al. |
| 2007/0173761 A1 | 7/2007 | Kanderian, Jr. et al. |
| 2007/0179444 A1 | 8/2007 | Causey et al. |
| 2007/0239114 A1 | 10/2007 | Edwards et al. |
| 2007/0287958 A1 | 12/2007 | McKenzie et al. |
| 2007/0287985 A1 | 12/2007 | Estes et al. |
| 2008/0058719 A1 | 3/2008 | Edwards et al. |
| 2008/0091176 A1 | 4/2008 | Alessi et al. |
| 2008/0106431 A1 | 5/2008 | Blomquist |
| 2008/0125701 A1 | 5/2008 | Moberg et al. |
| 2008/0139910 A1 | 6/2008 | Mastrototaro et al. |
| 2008/0183060 A1 | 7/2008 | Steil et al. |
| 2008/0215006 A1 | 9/2008 | Thorkild |
| 2008/0249468 A1 | 10/2008 | Edwards et al. |
| 2008/0306436 A1 | 12/2008 | Edwards et al. |
| 2008/0312512 A1 | 12/2008 | Brukalo et al. |
| 2008/0319383 A1 | 12/2008 | Byland et al. |
| 2009/0054867 A1 | 2/2009 | Gravesen et al. |
| 2009/0062747 A1 | 3/2009 | Saul |
| 2009/0088689 A1 | 4/2009 | Carter |
| 2009/0088692 A1 | 4/2009 | Adams et al. |
| 2009/0093772 A1 | 4/2009 | Genosar et al. |
| 2009/0182277 A1 | 7/2009 | Carter |
| 2009/0202608 A1 | 8/2009 | Allessi et al. |
| 2009/0220358 A1 | 9/2009 | Krivsky et al. |
| 2009/0240232 A1 | 9/2009 | Gonnelli et al. |
| 2009/0247982 A1 | 10/2009 | Krulevitch et al. |
| 2009/0281528 A1 | 11/2009 | Grovender et al. |

FOREIGN PATENT DOCUMENTS

| | | |
|---|---|---|
| DE | 3634725 A1 | 4/1998 |
| EP | 0209677 A1 | 1/1987 |
| EP | 0401179 A1 | 12/1990 |
| EP | 0513879 A2 | 11/1992 |
| EP | 0098592 A2 | 1/1994 |
| EP | 0638324 A1 | 2/1995 |
| EP | 0937475 A2 | 8/1999 |
| EP | 0902696 B1 | 3/2002 |
| EP | 1173197 B1 | 12/2004 |
| EP | 1512410 A1 | 3/2005 |
| EP | 1210136 B1 | 1/2006 |
| GB | 2054381 | 2/1981 |
| JP | 62270167 | 11/1987 |
| NL | 7310455 A | 2/1974 |
| RU | 2248223 C2 | 3/2005 |
| WO | 9728835 | 8/1997 |
| WO | 8503232 A1 | 1/1998 |
| WO | 9808871 A1 | 3/1998 |
| WO | 9810129 A1 | 12/1998 |
| WO | 9947161 A1 | 9/1999 |
| WO | 9948546 A | 9/1999 |
| WO | 0066138 A2 | 11/2000 |
| WO | 0066142 A2 | 11/2000 |
| WO | 0100223 A2 | 1/2001 |
| WO | 0187322 A2 | 11/2001 |
| WO | 02085406 A1 | 10/2002 |
| WO | 03008023 A1 | 1/2003 |
| WO | 03050846 A3 | 6/2003 |
| WO | 03061362 A2 | 7/2003 |
| WO | 03080160 A1 | 10/2003 |
| WO | 2004037195 A2 | 5/2004 |
| WO | 2004089335 A2 | 10/2004 |
| WO | 2004/094823 A2 | 11/2004 |
| WO | 2005046716 A1 | 5/2005 |
| WO | 2005048952 A2 | 6/2005 |
| WO | 2005060986 A1 | 7/2005 |
| WO | 2007051139 A2 | 5/2007 |
| WO | 2007129317 A1 | 11/2007 |
| WO | 2008036509 A3 | 3/2008 |
| WO | 2008139458 A3 | 11/2008 |
| WO | 2009013735 A1 | 1/2009 |
| WO | 2009016637 A1 | 2/2009 |
| WO | 2009081403 A2 | 7/2009 |
| WO | 2009125398 A2 | 10/2009 |

OTHER PUBLICATIONS

Office Action for U.S. Appl. No. 12/336,395 dated Sep. 21, 2011.

Gonnelli, Robert R. Barnett International Needle-Free Injection Systems presentation materials, Mar. 25, 2004, BioValve Technologies, Inc. (10 pages).

Banks et al., Brain uptake of the glucago-like peptide-1 antagonist exendin(9-39) after intranasal administration. J Pharmacol Exp. Ther. 309(2): 469-75, 2004.

Capaldi, Treatments and devices for future diabetes management. Nurs Times. 101(18): 30-2, 2005.

Choi et al., Control of blood glucose by novel GLP-1 delivery using biodegradable triblock copolymer of PLGA-PEG-PLGA in type 2 diabetic rats. Pharm Res. 21(5): 827-31, 2004.

Donahey et al., Intraventricular GLP-1 reduces short-but not long-term food intake or body weight in lean and obese rats. Brain Res. 779(1-2): 75-83, 1998.

Drucker, Development of glucagon-like peptide-1 based pharmaceuticals as therapeutic agents for the treatment of diabets. Curr Pharm Des. 7(14): 1399-412, 2001.

Gappa et al., The effect of zinc-crystallized glucagon-like peptide-1 on insulin secretion of macroencapsulated pancreatic islets. Tissue Eng. 7(1): 35-44, 2001.

Haak, New developments in the treatment of type 1 diabetes mellitus. Exp Clin Endocrinol Diabetes. 107 Suppl 3: S108-13, 1999.

Holst et al., On the treatment of diabetes mellitus with glucagon-like peptide-1. Ann N Y Acad Sci. 865: 336-43, 1998.

Hui et al., The short half-life of glucagon-like peptide-1 in plasma does not reflect its long-lasting beneficial effects. Eur J Endocrinol. 146(6): 863-9, 2002.

Joseph et al., Oral delivery of glucagon-like peptide-1 in a modified polymer preparation normalizes basal glycaemia in diabetic db/db mice. Diabetologia. 43(10); 1319-28, 2000.

Toft-Nielsen et al., Continuous subcutaneous infusion of glucagon-like peptide 1 lowers plasma glucose and reduces appetite in type 2 diabetic patients. Diabetes Care. 22(7): 1137-43, 1999.

Wang et al., Glucago-like peptide-1 can reverse the age-related decline in glucose tolerance in rats. J Clin Invest. 99 (1): 2883-9, 1997.

International Search Report for PCT/US2005/023818 dated Nov. 18, 2005.

International Search Report for PCT/US2007/65363 dated Sep. 18, 2008.

Office Action for U.S. Appl. No. 11/175,990 dated Nov. 10, 2009.

(56) References Cited

OTHER PUBLICATIONS

Office Action for U.S. Appl. No. 12/295,173 dated Jan. 26, 2010.
Singapore Written Opinion from Singapore Pat. App. No. 2008070302-5 dated Jan. 6, 2010.
USPTO Non-Final Rejection mailed Jun. 10, 2010 in connection with U.S. Appl. No. 12/295,173.
International Search Report and Written Opinion mailed Dec. 10, 2010 in connection with International Application No. PCT/US10/52352.
English Translation of First Office Action issued in connection with Chinese Application No. 200780020245.9.
First EPO Examination Report issued in connection with European Application No. 01988242.2.

* cited by examiner

HYDRAULICALLY ACTUATED PUMP FOR FLUID ADMINISTRATION

REFERENCE TO RELATED APPLICATIONS

The present application is a continuation of U.S. application Ser. No. 12/336,363, filed Dec. 16, 2008, now U.S. Pat. No. 8,080,726, which is a continuation of U.S. application Ser. No. 10/831,354, filed Apr. 23, 2004, now U.S. Pat. No. 7,530,968, which claims the benefit of U.S. Application No. 60/465,070, filed on Apr. 23, 2003, all of which are expressly incorporated herein by reference in their entirety.

BACKGROUND OF THE INVENTION

The systems and methods described herein relate to a hydraulic pump system that can be used in medicament pumps for injectables, specifically to low-cost, miniature, single-use pump systems.

Various people, such as diabetics, require continuous or near continuous infusion of certain drugs or medicines (broadly referred to herein as medicaments).

Many attempts have been made to provide continuous or near continuous dosing of medicaments, such as insulin, using pump systems. For example, one known pumping technique uses gas generated by various means to advance a plunger in a syringe, thereby injecting the medicament through an infusion set. The infusion sets is a means for conveying medicament through the patient skin and may comprise a standard needle, a microneedle, a microneedle array, and a catheter and cannula system.

Although these systems can work quite well, patients using these systems, particularly in continuous dose mode, need to monitor closely or deactivate these devices under circumstances where the ambient air pressure may vary greatly, such as in an airplane. In particular, patients need to be careful that the infusion pump does not deliver a dangerously increased dosage in airplanes at high altitudes, where the ambient pressure is significantly reduced.

What is needed is a simple, inexpensive, single-use only medicament pump system. Such a system must have the capacity to provide variable dosing under patient control as well as safety and consistency in the metered dose at any range of ambient pressures or operating conditions.

SUMMARY

In an exemplary embodiment, the systems described herein include, inter alia, a pump device, which may be single use, and that provides for sustained low volume (preferably high potency) medicament application, such as for use by insulin-dependent diabetics and other patients. The pump may employ as an actuator a spring-compressed bellows crank, hinged plate, paired roller set, or other peristaltic mechanisms to force a volume of hydraulic fluid through a flow restrictor, such as an aperture, thereby expanding one chamber of a two chamber hydraulic cylinder. The second (fluid storage) chamber, containing a medicament, is vented through a conventional orifice as the hydraulic chamber is expanded by introduction of additional hydraulic fluid. The medicament thus expelled may then be injected or infused into a patient via any suitable injection and/or infusion mechanism.

The restrictor, in one embodiment, may be a hydraulic fluid aperture and may be a fixed micro-aperture of approximately 0.1-10 μm in diameter, or about 1-5 μm in diameter, and one ten-thousandths of an inch (0.0001", or about 2.5 μm) in diameter. In another embodiment, the hydraulic fluid aperture may be an adjustable aperture providing either continuous orate p-wise diameter variations of approximately 0.1-10 μm in diameter, or about 1-5 μm in diameter, preferably one ten-thousandths of an inch (0.0001", or about 2.5 μm) in diameter. Combined with a hydraulic fluid of appropriate viscosity, the micro-aperture provides precise pressure regulation that is insensitive to ambient pressure or other environmental conditions. This insensitivity, in turn, allows for highly accurate dosing and dose regulation under a wider range of conditions than previously seen in the arts.

Thus one aspect of the invention provides a hydraulically actuated fluid delivery system for sustained delivery of a liquid component, comprising: a pump chamber, and a fluid storage chamber having an orifice and being functionally connected to said pump chamber by a moveable barrier; a hydraulic fluid reservoir for storing a high viscosity fluid, said reservoir being connected to said pump chamber, via a restrictor, such as an aperture, which may be less than 10 μm in diameter, and the largest insoluble particle, if any, in said hydraulic fluid may optionally be no more than the size of said aperture; and, an actuator functionally connected to said hydraulic fluid reservoir to cause said hydraulic fluid to flow into said pump chamber through said aperture, thereby expanding the volume of said pump chamber, displacing said moveable barrier and causing a quantity of said liquid component stored in said fluid storage chamber to be delivered at a sustained rate.

In one embodiment, the pump chamber and the fluid storage chamber are both within a compartment.

In one embodiment, the moveable barrier is a piston or plunger plate.

In one embodiment, the movement of the piston or plunger plate is guided such that the piston or plunger plate does not flip or generate leakage when moving.

In one embodiment, the moveable barrier is one or more deformable membranes separating the pump and the fluid storage chambers.

In one embodiment, the liquid component is a medicament, and the wall of the fluid storage chamber is composed of bio-inert materials.

In one embodiment, the aperture has a fixed size.

In one embodiment, the aperture is adjustable in size to allow variable hydraulic pressure.

In one embodiment, the size of the aperture is adjusted by a thumbwheel control/dial.

In one embodiment, the thumbwheel control activates a miniaturized valve or iris device.

In one embodiment, the quantity of said liquid component is expelled at a rate selected from: about 100 nl-1 μl per minute, about 1-10 μl per minute, or about 10-100 μl per minute.

In one embodiment, the actuator is a miniaturized bellows crank, paired rollers, one or more piezoelectric elements, a ratchet or stepper motor driven unit, a two-plate hinged peristaltic mechanism, an electrically driven or piezoelectric mechanism.

In one embodiment, the actuator employs one or more external springs having a constant spring coefficient over its full range of motion.

In one embodiment, the fluid delivery system further comprises a connective passage linking the hydraulic fluid reservoir to the pump chamber through the aperture.

In one embodiment, the liquid component is a solution of a medicament.

In one embodiment, the medicament is insulin, an opiate, a hormone, a psychotropic therapeutic composition.

In one embodiment, the orifice of the fluid storage chamber is connected to an infusion set for delivering the liquid component to a patient.

In one embodiment, the patient is a mammalian patient selected from human or non-human animal.

In one embodiment, the infusion set is a needle, a lumen and needle set, a catheter-cannula set, or a microneedle or microneedle array attached by means of one or more lumens.

In one embodiment, the pump is manufactured with inexpensive material for single-use.

In one embodiment, the inexpensive material is latex-free and is suitable for use in a latex-intolerant patient.

In one embodiment, the inexpensive material is disposable or recyclable.

In one embodiment, the inexpensive material is glass or medical grade PVC.

In one embodiment, the fluid delivery system further comprises a second hydraulic reservoir.

In one embodiment, the second hydraulic reservoir is separately and independently controlled by a second actuator.

In one embodiment, the second hydraulic reservoir and the original reservoir are both connected via a common connective passage and through the aperture to the pump chamber.

In one embodiment, the second hydraulic reservoir is connected to the pump chamber through a second aperture.

In one embodiment, one of the two hydraulic reservoirs is used for sustained delivery of the liquid component, and the other of the two hydraulic reservoir is used for a bolus delivery of the liquid component at predetermined intervals.

In one embodiment, both apertures are independently adjustable.

In one embodiment, one of the two apertures are adjustable.

In one embodiment, the sustained delivery is over a period of: more than 5 hours, more than 24 hours, more than 3 days, or more than one week.

In one embodiment, the viscosity of the hydraulic fluid is at least about ISO VG 20, or at least about ISO VG 32, or at least about ISO VG 50, or at least about ISO VG 150, or at least about ISO VG 450, or at least about ISO VG 1000, or at least about ISO VG 1500 or more.

Another aspect of the invention provides a hydraulically actuated pump system comprising: a pump chamber functionally connected to a moveable barrier; a hydraulic fluid reservoir for storing a high viscosity fluid, said reservoir being connected to said pump chamber via an aperture of less than 10 and in some embodiments less than 3 μm in diameter, and the largest insoluble particle, if any, in said hydraulic fluid is no more than the size of said aperture; and, an actuator functionally connected to said hydraulic fluid reservoir to cause said hydraulic fluid to flow into said pump chamber through said aperture, thereby expanding the volume of said pump chamber, displacing said moveable barrier.

Another aspect of the invention provides a method of administering a medicament, comprising: compressing a hydraulic fluid reservoir to force said hydraulic fluid through a connection means; passing said hydraulic fluid through an adjustable aperture into a pump chamber, wherein said pump chamber is separated from an adjacent fluid storage chamber by a moveable barrier and wherein said fluid storage chamber is filled with a medicament; displacing said moveable barrier into said fluid storage chamber by filling said pump chamber with said hydraulic fluid, wherein said displacing causes a quantity of said medicament to be expelled from said fluid storage chamber through an output orifice.

In one embodiment, the passing is regulated by the adjustable aperture varying the flow of the hydraulic fluid and thus the quantity of the medicament expelled through the orifice.

In one embodiment, the method further comprises injecting a quantity of the medicament into a patient through an infusion set connected to the orifice.

In one embodiment, the compressing employs peristaltic compaction of the reservoir at a constant rate.

In one embodiment, the compressing employs peristaltic compaction of the reservoir at a variable rate.

In one embodiment, the method further comprises rapidly compressing a second hydraulic reservoir fluidly connected to the pump chamber to displace the moveable barrier and thus cause a bolus of the medicament to be expelled through the orifice.

In one embodiment, the method further comprises passing the hydraulic fluid from the second hydraulic reservoir through a second aperture into the pump chamber.

It should be understood that the individual embodiments described above are meant to be freely combined with one another, such that any particular combination may simultaneously contain two or more features described in different embodiments whenever appropriate. In addition, all embodiments described for one aspect of the invention (such as device) also applies to other aspects of the invention (e.g. method) whenever appropriate.

BRIEF DESCRIPTION OF THE DRAWINGS

The present disclosure may be better understood and its numerous features and advantages made apparent to those skilled in the art by referencing the accompanying drawings.

The use of the same reference symbols in different drawings indicates similar or identical items.

DETAILED DESCRIPTION

Described herein is a drug delivery system, uses thereof and methods for making the same. In one embodiment, the systems described herein provide pump devices for delivering a medicant, agent, fluid or some other material to a patient, typically through the skin. To this end, the system includes an actuator that operates on a reservoir of viscous fluid. The actuator causes the viscous fluid to apply pressure to the medicant being delivered. The viscous fluid is controlled by a restrictor that, in one practice, controls the rate of flow of the fluid so that an uneven application of pressure to the reservoir is mediated, and a controlled rate of fluid movement is achieved. This controlled rate of fluid movement is employed to cause a medicant to be delivered at a selected rate.

In one embodiment the systems and methods described herein include a hydraulic pump system that may include a chamber (the "pump chamber") that can be filled with high viscosity fluid, which, when forced by pressure, enters the pump chamber through a restrictor, for example an opening/aperture, which is dimensionally adapted to control the rate of fluid flow therethrough. In one embodiment, the aperture is about the size of a 1-100 μm diameter circle (but not necessarily circular in shape). However, those of skill in the art will understand that any suitable restrictor may be employed, and that the size and the shape of the restrictor can vary to achieve the desired flow rate of the fluid being mediated under the expected conditions, including temperature and ambient pressure.

The increase in volume of the working fluid inside the pump chamber triggers the movement of a barrier mechanism, which can be coupled to other devices, such as a second (fluid storage) chamber.

One advantage of the instant hydraulic pump system resides with the restrictor through which the high viscosity working fluid flows. For example, when the restrictor is an aperture, when subjected to varying pressure, the working fluid enters the chamber through the aperture at a slow, yet relatively constant rate, thus mostly eliminating the potentially large variations in the force generating the pressure, while ensuring a substantially less variable expansion in volume of the working fluid in the chamber. This in turn leads to a relatively smooth and constant movement of the coupled barrier mechanism.

An additional advantage of the hydraulic pump system is that its relatively low requirement for a constant pressure source, or its high ability to tolerate relatively large variations in force generated by the pressure source. This is especially useful in manufacturing simple and inexpensive devices, such as single-use, disposable devices for medical use.

Partly because of the over-pressure employed in the hydraulic pump system, a further advantage is that the hydraulic pump is relatively insensitive to environmental changes, such as ambient temperature, altitude, or external pressure.

Figure 1:
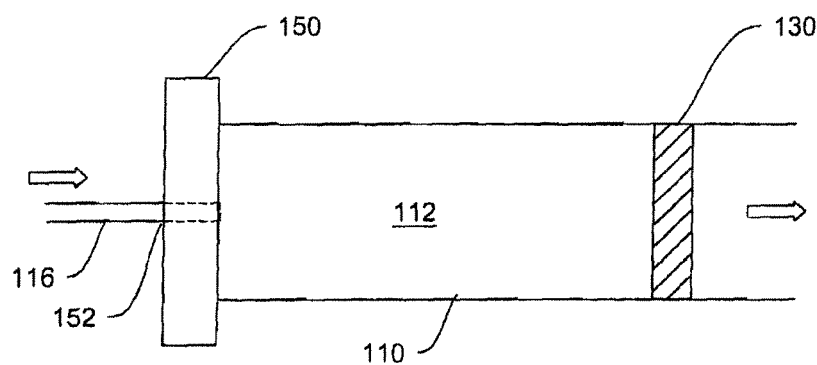
FIG. 1 is a high-level functional schematic drawing of a hydraulic pump system, according to one embodiment of the invention.

An illustrative embodiment of the hydraulic fluid system described herein is shown in the high-level functional drawing of FIG. 1. The pump chamber 110 may be shaped like, but is not limited to, a cylinder. The hatched lines represent a moveable barrier 130, which may (but need not to) be at the distal end of aperture 152. Hydraulic fluid 112 enters aperture 152 on pump chamber wall 150 into pump chamber 110, optionally via a connective passage 116.

As used herein, the term "ultrapure" is understood to encompass, although not be limited to, a fluid wherein the largest insoluble impurity particle in the working fluid is smaller than the aperture size (which may be for example about 2-3 μm in diameter, but could be smaller or larger, and may be adjustable). In those embodiments wherein the restrictor is an aperture, the aperture need not be circular in shape, and could be an oval, a square, a rectangle, a triangle, a polygon, or irregular in shape. In those embodiments wherein the restrictor is a tube, valve, sieve, or other mechanism or combination of mechanisms, the size and shape of the restrictor may be determined empirically by testing the fluid flow of selected fluids at conditions of interest. In one particular embodiment, the largest impurity particle is no more than 1 mm in diameter, or no more than 500 nm in diameter, or no more than 100 nm in diameter. In addition, the total amount of insoluble impurity particle is less than 0.1%, or 0.01%, or 0.001% in volume.

Viscosity is ordinarily expressed in terms of the time required for a standard quantity of the fluid at a certain temperature to flow through a standard orifice. The higher the value, the more viscous the fluid. Since viscosity varies inversely with temperature, its value is less meaningful unless accompanied by the temperature at which it is determined. As used herein, "high viscosity" means the working fluid has a viscosity grade of at least about ISO VG 20, or at least about ISO VG 32, or at least about ISO VG 50, or at least about ISO VG 150, or at least about ISO VG 450, or at least about ISO VG 1000, or at least about ISO VG 1500.

The hydraulic pump system can be employed in a fluid delivery system that can be manufactured inexpensively, and could take advantage of the slow, yet relatively constant delivery rate associated with the hydraulic pump system. Partly due to the slow rate of delivery, the fluid delivery system can be used to continuously deliver a fluid over a long period of time, e.g. 6 hrs, 12 hrs, 1 clay, 3 days, 5 days, 10 days, one month, etc. The fluid delivery system comprises the hydraulic pump, coupled to a separate chamber for storing fluid to be delivered (the "fluid storage chamber" or "fluid chamber" in short). There could be various mechanisms coupling the movement of the barrier mechanism in the hydraulic pump to the fluid chamber, such that a small amount of fluid (ideally equal to, or at least proportional to the amount of the working fluid entering the hydraulic pump chamber) is expelled from the fluid chamber, through one or more orifice, in response to the movement of the barrier.

One embodiment of the fluid delivery system is illustrated in a high-level schematic drawing in FIG. 2 (see detailed description below). This type of fluid delivery system/device can be used for a broad range of applications, including but are not limited to biomedical research (e.g. microinjection into cells, nuclear or organelle transplantation, isolation of single cells or hybridomas, etc.), and clinical applications (administration of medicaments, etc.).

For example, to provide a low level or variable dose of medicine over a long period of time (e.g., hours or even days), the fluid delivery system may form a portion of a single-use dispenser for a medicament to be applied through any of the standard infusions sets available on the market today or likely to be available in the future. The fluid delivery system, formed in some embodiments as low-cost plastic parts, may comprise a hydraulic cylinder containing two chambers, one function as the pump chamber described above, the other the fluid chamber for storing medicaments. In those embodiments, the hydraulic cylinder may be configured similarly to most conventional hydraulic cylinders, and the wall, especially the inner wall of at least the chamber for storing a liquid medicament to be delivered, may be composed of bio-inert and inexpensive materials.

The following description is for principal illustration only and should not be construed as limiting in any respect. Various illustrative alternative embodiments are described further below.

Figure 2:
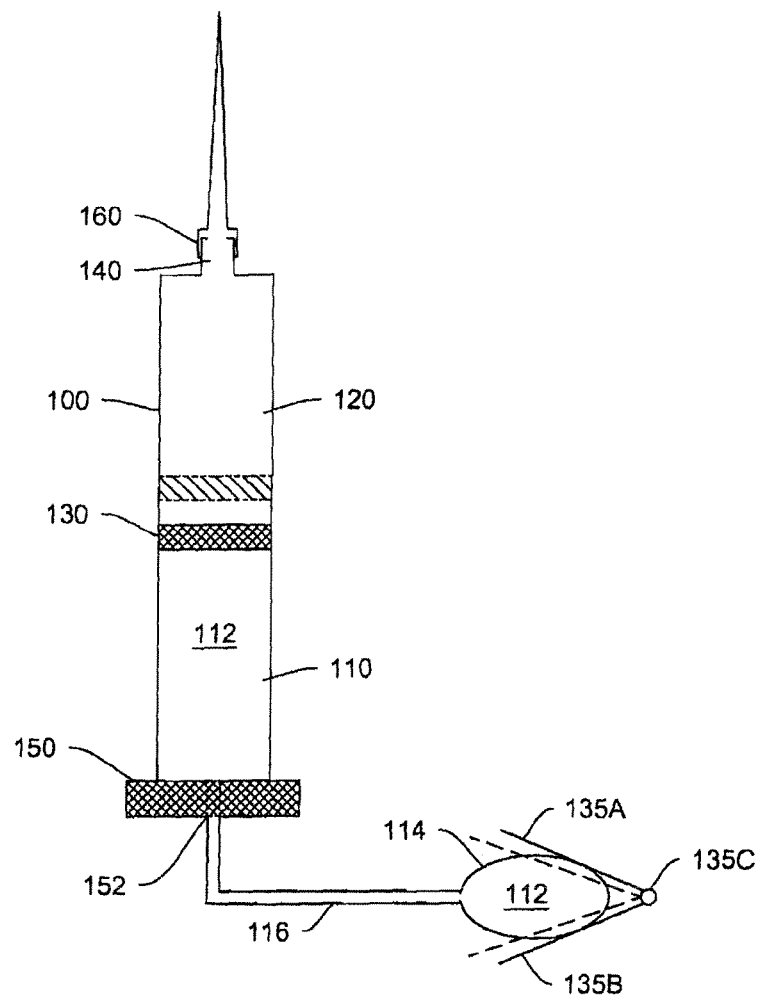
FIG. 2 is a high-level functional schematic drawing of a fluid delivery system comprising the hydraulic pump system, according to one embodiment of the invention.

Hydraulic cylinder 100, as described in FIG. 2, consists of two chambers, 110 and 120. Chamber 110 (corresponding to the pump chamber) is filled by hydraulic working fluid 112 from a hydraulic reservoir 114. Filling is accomplished by means of a connective passage 116, such as (but not limited to) a tube or lumen either flexibly or rigidly connecting hydraulic reservoir 114 and hydraulic cylinder 100. As hydraulic fluid 112 is forced out of reservoir 114 by actuator 135 (consisting, in an exemplary embodiment, of peristaltic compression plates 135A and 135B and hinge 135C), chamber 110 fills with hydraulic fluid expanding its volume and thus forcing piston element 130 (barrier mechanism) into chamber 120 (corresponding to the fluid chamber). The dotted lines in the actuator and the piston in FIG. 2 represent the later-in-time position of a plate-hinge actuating mechanism, and the later-in-time position of the barrier/piston.

Figure 3A:
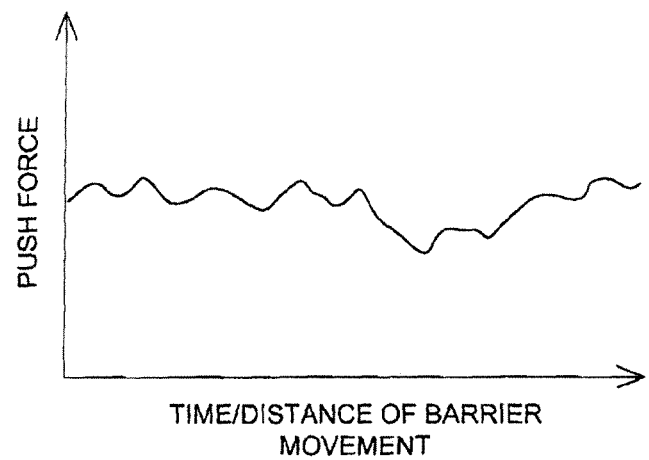
FIGS. 3A-3B are schematic drawings illustrating one of the advantages of the fluid delivery system comprising the hydraulic pump system.
Figure 3B:
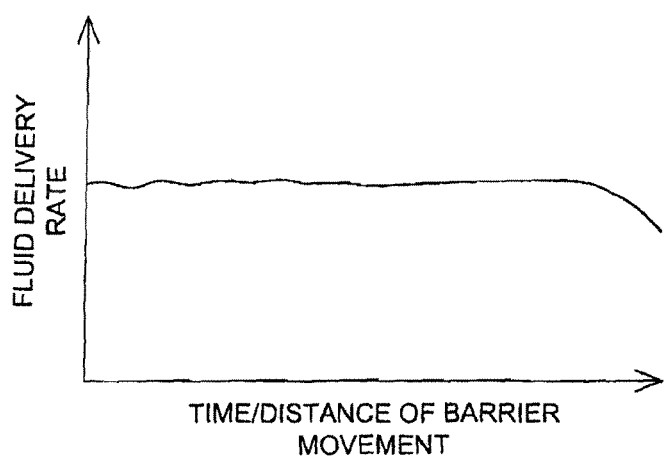

FIG. 3 is a schematic diagram illustrating one advantage of the fluid delivery system, e.g., its ability to tolerate relatively large variations in force generating the over-pressure, to create a relatively constant fluid delivery rate over time or distance traveled by the barrier piston. It is apparent that without the hydraulic pump system, any direct use of force to expel fluid in the fluid chamber will be hard to control, and will be subjected to a large variation in delivery rate of the fluid (FIG. 3A). In contrast, with the hydraulic pump, the delivery rate is much more constant (FIG. 3B).

Chambers 110 and 120 can be, but are not necessarily separate, physical chambers, since both chambers can exist within the confines of a hydraulic cylinder such as the one in FIG. 2 (hydraulic cylinder 100). The chambers are separated by a moveable barrier, such as the piston element 130 in FIG. 2, where piston 130 may be a fluid-tight barrier that prevents hydraulic fluid 112 from entering the second medicament fluid storage chamber 120. However, the invention is not limited in the type of hydraulic cylinder 100 or the contours, dimensions or finishes of the interior surfaces of cylinder 100, chamber 110, or chamber 120. Furthermore, the invention is not limited to particular configurations of piston element 130. The following description illustrates several of many possible alternative embodiments that can be employed in the subject fluid delivery system.

Figure 4A:
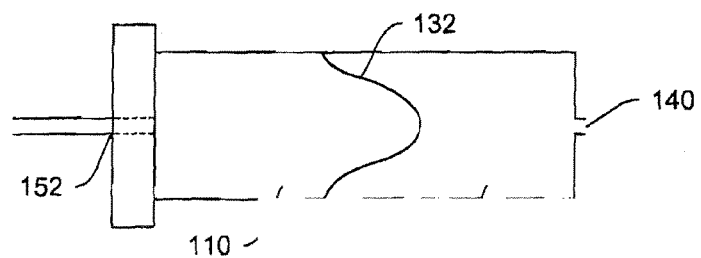
FIGS. 4A-4C are high-level functional schematic drawings of several fluid delivery system with various barriers.

In one embodiment, as shown in FIG. 4A, the piston element 130 in FIG. 2 is replaced by a flexible membrane 132 separating the pump chamber 110 and the fluid chamber 120. The flexible membrane can expand in response to the increased pressure from the pump chamber 110, due to the increase in volume of the working fluid entering the pump chamber 110 through aperture 152. This in turn expels fluid from the fluid chamber 120 via orifice 140.

Figure 4B:
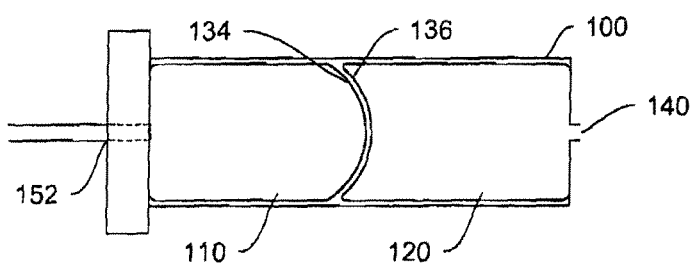

In another embodiment, as shown in FIG. 4B, chambers 110 and 120 may each have a separate wall unit 134 and 136, respectively (such as expandable bags made from flexible materials). By virtue of being within the limited confinement of cylinder 100, the expansion in volume of chamber 110 necessarily leads to the decrease in volume of chamber 120, creating a force to expel liquid from chamber 120 via orifice 140.

Figure 4C:
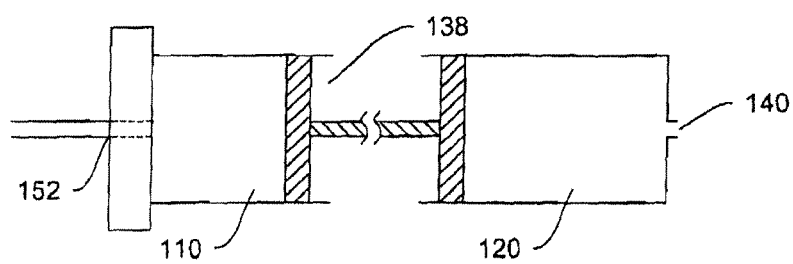

In yet another embodiment, as shown in FIG. 4C, the pump chamber 110 and the fluid chamber 120 may be separated from each other, but are mechanically coupled through a barrier mechanism 138 that transmits movements in pump chamber 110 to that in the fluid chamber 120. The coupling mechanism 138 can either augment or diminish the magnitude of the initial movement in the pump chamber 110, such that the corresponding movement in the fluid chamber 120 is increased, or decreased, respectively, resulting in expelling a larger or smaller amount of medicament fluid from the fluid chamber 120. For example, the coupling mechanism 138 can be two pistons linked by a shaft, as shown in FIG. 4C. In one embodiment, the fluid chamber 120 may be detached from the pump chamber 110, so that a new fluid chamber (120', not shown) may be re-attached.

As noted above, chamber 120 is to be initially filled with a quantity of liquid component to be delivered, such as a medicament. In the case of a medicament, the quantity would typically be determined by a medical professional in order to provide the necessary dosing over a pre-determined period of time. The volume of the fluid chamber may be about 100 μl, 500 μl, 1 ml, 3 ml, 5 ml, 10 ml, 30 ml, 50 ml, 100 ml or more.

The depicted hydraulic cylinder 100 in FIG. 2 can be further connected to an infusion set 160 through orifice 140 at the distal end of chamber 120 (distal here meaning the end of chamber 120 distant from piston 130). In other words, the output orifice 140 of hydraulic cylinder 100 is on the opposite end of the cylinder from hydraulic fluid input aperture 152, as one would commonly expect in a hydraulic system. However, this is merely one of the preferred designs. The output orifice 140 could be located on the wall of cylinder 100 at the chamber 120 portion if desired (see FIG. 5 below).

Attached to orifice 140, in some embodiments, is an infusion device or "set" 160 selected from any of the infusion means conventionally known and used in the medical arts. Examples of infusion devices include: a needle, such as depicted in FIG. 1; a lumen and needle set; a catheter-cannula set; or a microneedle or microneedle array attached by means of one or more lumens. One of ordinary skill in the art will readily appreciate that many devices exist to convey medicaments into a body. Accordingly, the invention is not limited in the types of infusion or injection devices used therewith.

Figure 5:
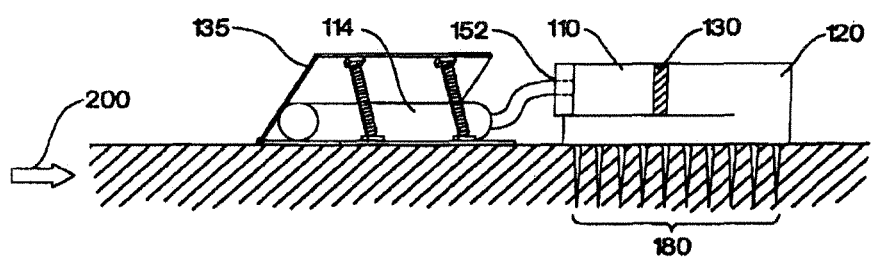
FIG. 5 is a high-level functional schematic drawing of an alternative fluid delivery system, according to one embodiment of the invention. The alternative fluid delivery system in this embodiment features arrayed microneedles on an transdermal patch.

In an illustrative embodiment, as shown here in a high-level schematic drawing in FIG. 5, the fluid delivery system is affixed to a delivery area of a patient, e.g. skin 200, by an adhesive means, such as a transdermal patch. The fluid chamber 120 is connected to a microneedle or an array of microneedles 180, such as those described in U.S. Pat. No. 6,503,231 (incorporated herein by reference). Unlike what is shown in FIG. 5, the microneedle(s) need not completely enter the skin layer 200. To achieve a low profile, both the pump chamber 110 and the fluid chamber 120 may be flat in shape (rather than shaped like a cylinder), and the outer-surfaces may hug the contour of the attached skin layer 200. The orifice(s) (not shown) connecting the fluid chamber and the microneedle(s) preferably opens on a side-wall of the fluid chamber 120. Alternatively, a connective passage may link the orifice on fluid chamber 120 to the microneedle or microneedle(s) array. Barrier 130 and aperture 152 are as described above. Also shown is one embodiment of the actuator, where plates 135 actuated by spring mechanism squeeze the hydraulic fluid reservoir 114 to inject hydraulic working fluid into the pump chamber 110. Other actuators, such as those described in other parts of the specification, may be adapted for use in this embodiment.

As exemplified in FIG. 2, in operation, the fluid (e.g. medicament) is administered by compressing hydraulic fluid reservoir 114 in a controlled manner with actuator 135. FIG. 2 shows an exemplary peristaltic mechanism actuator 135. However, the actuator may be alternatively selected from any of a number of squeeze devices that apply a force on the reservoir, such as a miniaturized bellows crank or paired rollers bearing on reservoir 114 (see FIG. 6 below). Moreover, in other embodiments, the reservoir can be acted on by an expanding gas volume, thermal energy, or any other device or process that will be capable of causing the fluid to apply a pressure, either directly or indirectly, to the medicant being delivered.

In the embodiment shown in FIG. 2, plates 135A and 135B are attached by hinge 135C and forced together by means of a spring or, in some embodiments, one or more piezoelectric elements, such that flexible (e.g., elastomeric) hydraulic fluid reservoir 114 is squeezed between them. Squeezing an elastomeric reservoir forces the contents of the reservoir out through whatever aperture exists in the reservoir. In some embodiments, an aperture 152 is provided by the coupling tube 116 and the adjustable aperture 150, further described below.

Actuator 135 may also take on other forms. Ratchet or stepper motor driven units that compress plates or other structures bearing on hydraulic reservoir 114 that move hydraulic fluid may also be used without departing from the present invention. Additionally, for a two plate hinged peristaltic mechanism such as that represented by reference designator 135 in FIG. 2, springs mounted internally or externally to the plates (not shown) may be used to force the plates together. Electrically driven or piezoelectric mechanisms, such as those described in the prior art, may also be employed.

Figure 6A:
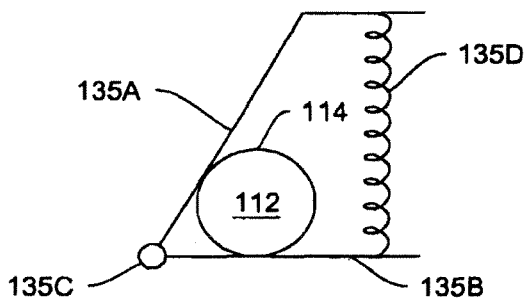
FIGS. 6A-6C are high-level functional schematic drawings of several actuator mechanisms that can be used with the fluid delivery system employing the hydraulic pump, according to one embodiment of the invention.

In one embodiment, as shown in FIG. 6A, one or more external spring(s) 135D having a constant spring coefficient over its full range of motion is (are) employed, (For the sake of simplicity, a single spring configuration is described. But multiple springs may be used to adjust forces.) This spring is disposed so as to connect portions of plates 135A and 135B distant from hinge 135C and to draw them together (inwardly), thus bearing on reservoir 114. Thus, when the system is initially prepared for use, the spring is extended (i.e., placed in tension) by forcing plates 135A and 135B apart. The plates are then held in place with a removable brace or other device (not shown) to keep them from compressing hydraulic reservoir 114. Once the pump is in place and connected through infusion means 160 (see FIG. 2, but not shown here) to inject the medicament into the patient, the brace may be removed. The constant spring tension placed on plates 135A and 135B of actuator 135 will then slowly force the plates together and squeeze hydraulic fluid 112 out of reservoir 114 in a peristalsis-like action.

Figure 6B:
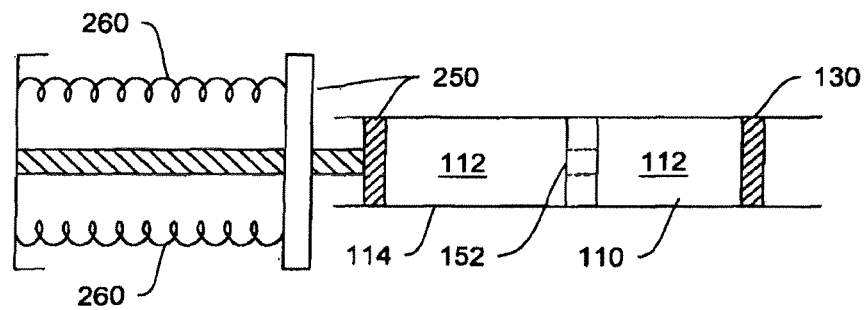
Figure 6C:
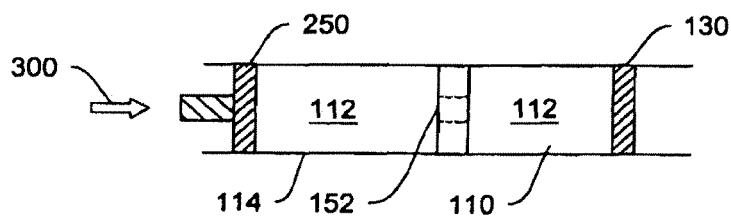

In another embodiment, as illustrated in FIG. 6B, a compressed spring or set of springs 260 may be used to push a piston element 250 through a guided-path to compress the hydraulic fluid reservoir 114. At the end of the reservoir, distal to the piston element 250, is an aperture 152 that allows the hydraulic fluid 112 to enter the adjacent pump chamber 110, so that barrier 130 may move accordingly. In a more simplified version, the spring mechanism 250 and 260 may be replaced by thumb force 300, just like in a traditional syringe (FIG. 6C). In both FIGS. 6B and 6C, there is no connective passage separating the fluid reservoir 114 from the pump chamber 110.

The adjustable aperture provides regulation of the hydraulic pressure and flow rate in the pump chamber 110. This regulation may be effected by allowing the aperture 152 (in FIG. 2) to be adjusted to extremely small dimensions, for example, to a diameter of one-ten thousandths of an inch (0.0001 inches, or about 2.5 µm) or less.

In one embodiment, the aperture 152 has a fixed size. It does not have to be round/circular in shape. For example, it could be roughly a square, a triangle, an oval, an irregular shape, or a polygon. Whatever the shape, the area of the opening will be sized to achieve the flow rate desired. In example, the opening may be about one-tenth thousandths of an inch (or 2-3 µm) in diameter. Depending on use, the opening size can be anything, including an opening between 200 nm-500 nm, or 500 nm-1000 nm, or 1-2 µm, or 5-10 µm. Other sizes and dimensions can be selected and the size and dimension selected will depend upon the application at hand.

Figure 7:
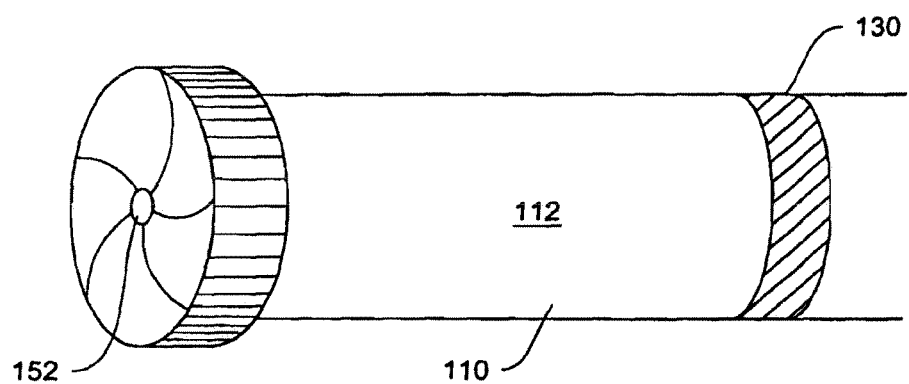
FIG. 7 is a high-level functional schematic drawing of the adjustable control for aperture opening size.

In other embodiments, as shown in FIG. 7, the aperture 152 may be adjustable in size, as by means of a conventional iris mechanism (see FIG. 7), miniature valve, or paired gating slits (for example and not by way of limitation) currently known in the arts. For example, the adjustable aperture 152 may be adjusted by means of a simple thumb wheel 150 that activates the conventional, miniaturized valve or iris device discussed above. In an alternate embodiment, an electrical motor or piezoelectric device may be used to open or close the aperture, thus affecting the rate at which hydraulic fluid 112 flows into chamber 110 and moves barrier 130.

Regardless of whether the aperture is adjustable or not, the flow rate of the hydraulic fluid can be controlled to suit different needs. In certain embodiments, the quantity of the fluid in the fluid chamber is expelled at a rate selected from: about 100 nl-1 µl per minute, about 1-10 µl per minute, or about 10-100 µl per minute. In other embodiments, the fluid rate is mediated and controlled to be from 0.001 µl per hour to 100 milliliters per hour. The rate selected will depend upon the application at hand, and those of skill in the art will be able to determine the proper dosage rate for a given application.

One feature of aperture 152, whether adjustable or not, is that it can be made extremely small so that hydraulic fluid 112 enters chamber 110 at very low rates, such as but not limited to rates as low as ones or tens of micro-liters per minute. When used with a hydraulic fluid of appropriate viscosity (further discussed below), the configuration of aperture 152 enables precise pressure regulation that is insensitive to ambient pressure or other environmental conditions. This insensitivity, in turns, allows for highly accurate dosing and dose regulation under a wider range of conditions than previously seen in the arts.

Hydraulic fluid 112 is, in some embodiments, an ultrapure, high viscosity, bio-inert material. Viscosity is limited at its upper bound by the amount of force developed by the actuator. In certain embodiments, the force generated by the actuator is about 10 lb, 5 lb, 3 lb, 2 lb, 1 lb, 0.5 lb, 0.1 lb, 0.001 lb or less. At its lower bound, the fluid must be viscous enough so that the flow can remain highly regulated by the combination of actuator pressure and aperture diameter in all environment conditions, especially in the presence of low atmospheric pressure and/or high ambient temperature (where viscosity tends to decrease). A simple test may be performed to roughly determine the average flow rate of the hydraulic fluid, by fixing an aperture size and the pushing force exerted on the fluid reservoir, and determining the amount of hydraulic fluid remaining in the reservoir (and thus the amount exited) after a period of time. Consecutive periods of hydraulic fluid loss (e.g. fluid loss in consecutive 5-minute periods, etc.) may be measured to determine if the rate of hydraulic fluid loss from the reservoir is constant over time under the condition used.

Medicaments suitable for use with the system presently disclosed include: insulin, opiates and/or other palliatives, hormones, psychotropic therapeutic composition, or any other drug or chemical whose continuous low volume dosing is desirable or efficacious for use in treating patients. Note too that "patients" can be human or non-human animal; the use of continuous dosing pumps is not confined solely to human medicine, but can be equally applied to veterinarian medicines.

Figure 8A:
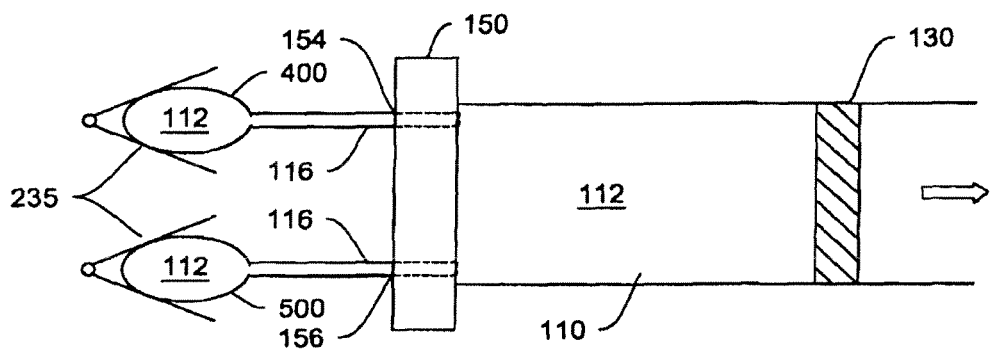
FIGS. 8A-8B are high-level functional schematic drawings of several fluid delivery systems with multiple actuators, according to embodiments of the invention.

In an alternate embodiment of the system, two or more hydraulic reservoirs and actuators are provided (FIG. 8). In an illustrative embodiment shown in FIG. 8A, the first reservoir 400 and actuator 235 are the same as or similar to items 114 and 135 in FIG. 2. The second reservoir 500 and actuator 235, which may use the same peristaltic actuator 135 as shown in FIG. 2 or any other conventional alternative, such as those described above, are provided with a separate control. In other words, the second actuator may be controlled independently of the first. Both fluid reservoirs are connected to the pump chamber wall 150, through apertures 154 and 156, respectively. The connection may optionally go through connective passages 116. Such a configuration is useful in situations where special, discrete doses of the medicament may be necessary. For example, an insulin-dependent diabetic may often find it necessary to receive an additional booster dose or bolus of insulin immediately after meals, in addition to and along with continuously supplied insulin during the day. The second actuator control may thus be operated independently of the first actuator control mechanism to deliver the bolus.

Figure 8B:
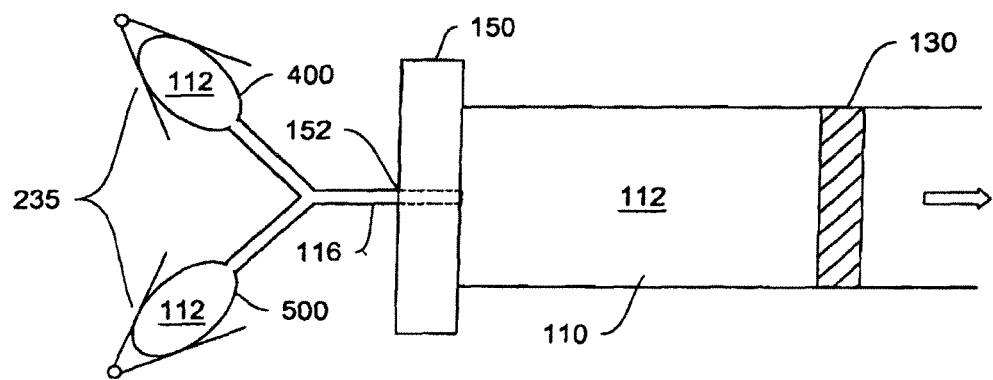

In an alternative embodiment, shown in FIG. 8B, hydraulic fluid 112 from both reservoirs 400 and 500 may pass together through a common lumen 116 and thence through adjustable aperture 152 (FIG. 8B). Alternatively, as described above, the two reservoirs may lead into hydraulic chamber 110 by way of separate lumens and separately adjustable apertures 154 and 156 (FIG. 8A). In this latter configuration, the rate of dosing affected by either reservoir may be independently controlled through their respective adjustable apertures.

In a further alternative, one of the reservoirs may lead to a fixed aperture while the other leads to an adjustable aperture. In this embodiment, useful in cases such as the insulin-dependent diabetic described above, the fixed-aperture-connected hydraulic reservoir can be actuated to provide bolus dosing at discrete intervals, while the adjustable-aperture-connected hydraulic reservoir can be used to provide continuous slow dosing.

Exemplary Embodiment of Using the Fluid Delivery System

In one exemplary embodiment, there is provided a method of administering a medicament, comprising: compressing a hydraulic fluid reservoir to force said hydraulic fluid through a connection means; passing said hydraulic fluid through an adjustable aperture into a first, pump chamber, wherein said pump chamber is separated from an adjacent fluid storage chamber, for example, by a moveable barrier, and wherein said fluid storage chamber is filled with a medicament; displacing said moveable barrier into said fluid storage chamber by filling said pump chamber with said hydraulic fluid, wherein said displacing causes a quantity of said medicament to be expelled from said fluid storage chamber through an orifice.

Said passing may be regulated by said adjustable aperture varying the flow of said hydraulic fluid and thus the quantity of said medicament expelled through said orifice. Furthermore, the method may further comprise injecting a quantity of said medicament into a patient through an infusion set connected to said orifice.

In some embodiments, the step of compressing may employ peristaltic compaction of said reservoir at a constant rate. Alternatively, the compressing step may employ peristaltic compaction of said reservoir at a variable rate.

In yet another alternate embodiment, the method may further comprise rapidly compressing a second hydraulic reservoir fluidly connected to said pump chamber to displace said moveable barrier and thus cause a bolus of said medicament to be expelled through said orifice. This embodiment may further comprise passing said hydraulic fluid from said second hydraulic reservoir through a second aperture into said pump chamber.

Alternate Embodiments

The order in which the steps of the present method are performed is purely illustrative in nature, and the steps may not need to be performed in the exact sequence they are described. In fact, the steps can be performed in any suitable order or in parallel, unless otherwise indicated as inappropriate by the present disclosure.

While several illustrative embodiments of the hydraulic pump system and its use in the fluid delivery system have been shown and described, it will be apparent to those skilled in the art that changes and modifications may be made without departing from this invention in its broader aspect and, therefore, the appended claims are to encompass within their scope all such changes and modifications as fall within the true spirit of this invention.

We claim:

1. A fluid delivery device comprising:
a hydraulic housing having a piston configured to sealingly slide along an inner wall of the hydraulic housing and separate the hydraulic housing into a hydraulic pump chamber and a fluid reservoir, the hydraulic pump chamber having a hydraulic fluid and configured to urge the piston along the inner wall to deliver a fluid in the fluid reservoir to a patient;
a first actuator;
a first hydraulic reservoir chamber having the hydraulic fluid and coupled between the first actuator and the hydraulic pump chamber, the first actuator being configured to urge the hydraulic fluid in the first hydraulic reservoir chamber into the hydraulic pump chamber;
a flow restrictor fluidly coupling the first hydraulic reservoir chamber and the hydraulic pump chamber;
a second hydraulic reservoir chamber having the hydraulic fluid and fluidly coupled with the hydraulic pump chamber; and
a second actuator configured to urge the hydraulic fluid from the second hydraulic reservoir chamber into the hydraulic pump chamber, independent of the first actuator.

2. The fluid delivery device of claim 1, wherein the flow restrictor and the first actuator are configured to transfer the hydraulic fluid from the first hydraulic reservoir chamber to the hydraulic pump chamber to deliver the fluid from the fluid reservoir at a sustained basal rate.

3. The fluid delivery device of claim 2, wherein the sustained basal rate is constant.

4. The fluid delivery device of claim 2, wherein the sustained basal rate is over a period of more than 5 hours.

5. The fluid delivery device of claim 2, wherein the sustained basal rate is over a period of approximately 24 hours.

6. The fluid delivery device of claim 1, wherein the first and second actuators are compression springs.

7. The fluid delivery device of claim 1, wherein the first and second actuators are coupled to the hydraulic pump chamber in parallel.

8. The fluid delivery device of claim 2, wherein the second actuator is configured to selectably transfer the hydraulic fluid from the second hydraulic reservoir chamber into the hydraulic pump chamber at discrete intervals to deliver a bolus dosage of the fluid in addition to the sustained basal rate.

9. The fluid delivery device of claim 1, wherein the first actuator includes two or more springs.

10. The fluid delivery device of claim 1 further comprising the fluid in the fluid reservoir, wherein the fluid comprises insulin.

11. The fluid delivery device of claim 1, wherein the hydraulic fluid has a viscosity of approximately ISO VG 1500 or more when in use.

12. The fluid delivery device of claim 1, further comprising a moveable piston separating the hydraulic pump chamber and the second actuator.

13. The fluid delivery device of claim 1, wherein the hydraulic pump chamber and the fluid reservoir are comprised of a polymer.

14. The fluid delivery device of claim 1, wherein the second hydraulic reservoir is positioned between the second actuator and the hydraulic pump chamber.

15. The fluid delivery device of claim 1, wherein the flow restrictor is a fixed aperture.

16. The fluid delivery device of claim 1, wherein the piston is a single piston that contacts the fluid in the fluid reservoir on one side and the hydraulic fluid on another side.

17. A fluid delivery device comprising:
   a hydraulic housing having a piston configured to sealingly slide along an inner wall of the hydraulic housing and separate the hydraulic housing into a hydraulic pump chamber and a fluid reservoir, the hydraulic pump chamber having a hydraulic fluid and configured to urge the piston along the inner wall to deliver a fluid in the fluid reservoir to a patient;
   a first hydraulic reservoir chamber having the hydraulic fluid;
   a fixed aperture flow restrictor fluidly coupling the first hydraulic reservoir chamber and the hydraulic pump chamber, the fixed aperture flow restrictor configured to control the rate the hydraulic fluid flows between the first hydraulic reservoir chamber and the hydraulic pump chamber;
   a first actuator coupled to the first hydraulic reservoir chamber and configured to continuously deliver the hydraulic fluid from the first hydraulic reservoir chamber to the hydraulic pump chamber for a period of time;
   a second hydraulic reservoir chamber fluidly coupled to the hydraulic pump chamber, independent of the first hydraulic reservoir chamber; and
   a second actuator coupled to the second hydraulic reservoir chamber and operable independent of the first actuator and at discrete intervals during the period of time to periodically deliver the hydraulic fluid from the second hydraulic reservoir chamber to the hydraulic pump chamber independent of and in addition to the continuous delivery of the hydraulic fluid from the first hydraulic reservoir chamber.

* * * * *